(12) United States Patent  (10) Patent No.: US 8,287,566 B2
Leopold et al.  (45) Date of Patent: Oct. 16, 2012

(54) SPRAY DEVICES AND METHODS

(75) Inventors: Phillip M. Leopold, North Barrington, IL (US); Allan Roberts, Lake Villa, IL (US)

(73) Assignee: Cohera Medical, Inc., Pittsburgh, PA (US)

( * ) Notice: Subject to any disclaimer, the term of this patent is extended or adjusted under 35 U.S.C. 154(b) by 1208 days.

(21) Appl. No.: 11/925,053

(22) Filed: Oct. 26, 2007

(65) Prior Publication Data

US 2009/0112255 A1  Apr. 30, 2009

(51) Int. Cl.
  *A61B 17/08* (2006.01)
  *A61D 1/00* (2006.01)
(52) U.S. Cl. ............................................. 606/214
(58) Field of Classification Search ............ 606/213, 606/214; 604/57, 68–72, 82, 191, 225, 272
  See application file for complete search history.

(56) References Cited

U.S. PATENT DOCUMENTS

| | | | |
|---|---|---|---|
| 3,559,652 A * | 2/1971 | Banitt et al. | 606/214 |
| 4,740,534 A | 4/1988 | Matsuda et al. | |
| 4,804,691 A | 2/1989 | English et al. | |
| 4,877,157 A * | 10/1989 | Saulle | 222/387 |
| 4,902,281 A * | 2/1990 | Avoy | 604/191 |
| 4,994,542 A | 2/1991 | Matsuda et al. | |
| 5,173,301 A | 12/1992 | Itoh et al. | |
| 5,542,934 A | 8/1996 | Silver | |
| 5,605,541 A | 2/1997 | Holm | |
| 5,674,921 A | 10/1997 | Regula et al. | |
| 5,740,965 A * | 4/1998 | Miyagi et al. | 239/423 |
| 5,759,171 A | 6/1998 | Coelho et al. | |
| 5,975,367 A | 11/1999 | Coelho et al. | |
| 6,059,749 A | 5/2000 | Marx | |
| 6,179,862 B1 | 1/2001 | Sawhney | |
| 6,206,905 B1 | 3/2001 | Holm et al. | |
| 6,454,786 B1 | 9/2002 | Holm et al. | |
| 6,613,020 B1 | 9/2003 | Holm et al. | |
| 6,884,230 B1 | 4/2005 | Epstein et al. | |
| 7,077,339 B2 | 7/2006 | Leach | |
| 7,129,210 B2 * | 10/2006 | Lowinger et al. | 424/1.69 |
| 7,264,823 B2 | 9/2007 | Beckman et al. | |
| 7,967,220 B2 * | 6/2011 | Hansen et al. | 239/304 |
| 2002/0161335 A1 * | 10/2002 | Metzner et al. | 604/191 |
| 2004/0170597 A1 | 9/2004 | Beckman et al. | |

FOREIGN PATENT DOCUMENTS

| | | |
|---|---|---|
| EP | 0 466 552 | 1/1992 |
| JP | 63 278924 | 11/1988 |
| WO | WO 02/26848 | 4/2002 |
| WO | WO 2004/009227 | 1/2004 |
| WO | WO 2005/118011 | 12/2005 |

OTHER PUBLICATIONS

European Patent Office, International Preliminary Report on Patentability for Application PCT/US2008/080428, dated Apr. 27, 2010, 14 pages.

International Search Report & Written Opinion, PCT/US2008/080428, mailed May 26, 2009, 14 pages.

* cited by examiner

*Primary Examiner* — Melanie Tyson

(74) *Attorney, Agent, or Firm* — Fish & Richardson P.C.

(57) ABSTRACT

Some embodiments of a spray device can be configured to maintain a viscous fluid in isolation from a propellant fluid until after the viscous fluid exits from a nozzle of the spray device. For example, the viscous fluid may include an adhesive such as surgical adhesive. When the spray device is actuated, the surgical adhesive can exit the nozzle so that the propellant fluid acts upon the surgical adhesive to break it into droplets for application on a targeted site.

6 Claims, 13 Drawing Sheets

SPRAY DEVICES AND METHODS

TECHNICAL FIELD

This document relates to spray devices for dispensing fluid materials, including viscous fluids such as some surgical adhesives.

BACKGROUND

Biological and synthetic tissue adhesives have been developed as alternatives to sutures and staples for adhering biological tissue. Examples of biological tissue adhesives include fibrin sealants, which can be used externally or internally for wound closure and sealing. Such fibrin sealants are typically formed using two reactive components that are combined in a chemical process, for example, immediately before dispensation from a double-barrel syringe.

SUMMARY

Some embodiments of a spray device can be configured to maintain a surgical adhesive or other viscous fluid in isolation from a propellant fluid until after the fluid exits from a nozzle of the spray device. When the spray device is actuated, the viscous fluid can exit the nozzle whereat the propellant fluid acts upon the viscous fluid to break it into droplets that are deposited at a targeted site. As such, the spray device can deliver the viscous fluid from a reservoir in the spray device to the targeted tissue without having to mix the propellant fluid or other materials with the viscous fluid prior to dispensation. Such a configuration can be useful for dispensing surgical adhesives having a relatively high viscosity.

In particular embodiments, a surgical adhesive spray device may include a nozzle device having a plurality of dispensation ports. The spray device can also include a housing that defines an interior space to receive at least two reservoirs. The spray device may further include a propellant reservoir arranged in the housing to be in fluid communication with at least one propellant dispensation port of the nozzle device. The propellant reservoir can contain a propellant fluid. The spray device may also include an adhesive reservoir arranged in the housing to be in fluid communication with an adhesive dispensation port of the nozzle device. The adhesive reservoir can contain a surgical adhesive that is isolated from the propellant fluid while in the spray device.

In other embodiments, a method of delivering a surgical adhesive to a targeted site may include manipulating a spray device so that a nozzle device is directed toward the targeted site. The method may also include dispensing a surgical adhesive from an adhesive reservoir arranged in the spray device, to a first output port of the nozzle device, and out of the spray device. The method may further include dispensing a propellant fluid from a propellant reservoir arranged in the spray device, to a second output port of the nozzle device, and out of the spray device. The propellant fluid can act upon the surgical adhesive that exits the first output port to form droplets of the surgical adhesive that advance toward the targeted site.

Some embodiments described herein include a spray device for dispensing droplets of a viscous fluid. The spray device may include a housing defining an interior space to receive a supply of a propellant fluid and a supply of a viscous fluid. The spray device may also include a first container arranged in the housing to maintain the supply of the viscous fluid in isolation from propellant fluid. The spray device may further include a nozzle device to spray droplets of the viscous fluid toward a targeted site. The nozzle device can be in fluid communication with the first container such that the viscous fluid interacts with the propellant fluid only after exiting the nozzle device.

Particular embodiments described herein include a disposable, single-use spray device for dispensing a surgical adhesive. The spray device may include a predetermined amount of a surgical adhesive contained in an adhesive reservoir. The spray device may also include a housing that defines an interior space for the adhesive reservoir. The spray device may further include an actuator coupled to the housing for adjustment by a user. The spray device may also include a nozzle device in fluid communication with the adhesive reservoir. The nozzle device can spray droplets of the surgical adhesive toward a single targeted site in response to user adjustment of the actuator. The entire spray device is disposable and non-reusable after the nozzle device sprays droplets of the surgical adhesive toward the single targeted site.

Certain embodiments include a method of delivering a surgical adhesive to a targeted tissue site. The method may include preparing a spray device that is a disposable and non-reusable device for use in a procedure on an individual patient. The spray device may contain a supply of a surgical adhesive. The method may also include actuating the spray device to spray droplets of the surgical adhesive toward a targeted tissue site on the individual patient. The method may further include discarding the spray device after the surgical adhesive is delivered to the targeted tissue site on the individual patient so that the spray device is non-reusable in a subsequent procedure for a different patient.

In some embodiments, a spray device packaging system may include a surgical storage module defining an interior space. The packaging system may also include a plurality of surgical adhesive spray devices that are each contained in individual trays or pouches and arranged fully within the interior space of the storage module. Each of the spray devices may include a housing that contains a supply of a propellant fluid and a supply of surgical adhesive, an actuator movably coupled to the housing, a nozzle device to spray droplets of the surgical adhesive in response to movement of the actuator.

Particular embodiments described herein include a method of manufacturing a surgical adhesive spray device. The method may include inserting a surgical adhesive into a spray device housing. The method may also include inserting a propellant fluid into the spray device housing. The surgical adhesive can be isolated from the propellant fluid. The method may further include arranging an adhesive flow path for passage of the surgical adhesive to a nozzle device. The method may also include arranging a propellant flow path for passage of the propellant fluid to the nozzle device such that the propellant flow path out of the nozzle device is separate from the adhesive flow path out of the nozzle device. The method may further include sealing the assembled spray device in a disposable storage package.

In some embodiments, a container for storing surgical adhesive may include a container housing having a movable plunger arranged therein. The container housing and the movable plunger may define a first internal space on a first side of the plunger and may define a second internal space on a second opposing side of the plunger. The container for storing surgical adhesive may also include a surgical adhesive disposed in the first internal space of the contain housing. The container may further include a bias instrument disposed in the second internal space to urge the movable piston toward the first internal space. The movable piston may provide a seal that separates the surgical adhesive from the bias instrument. The container may also include a fill port in communication with the first internal space to permit injection of the surgical adhesive to the first internal space. The container may further include an adjustable valve to controllably release the surgical adhesive from the first internal space. The bias instrument can cause the piston to move in the container housing when the adjustable valve releases the surgical adhesive from the first internal space.

Some of the embodiments described herein may provide one or more of the following advantages. First, the spray device can be used to deliver a viscous fluid, such as a surgical adhesive, to a targeted tissue site in a controlled and reliable manner. In such circumstances, the spray device may be operated by a surgeon or other medical practitioner to selectively dispense droplets of the surgical adhesive (e.g., when the surgeon or other medical practitioner activates an actuator on the spray device).

Second, the spray device can be used as a single-use instrument suitable for use in a surgical environment. For example, the spray device can be disposable and non-reusable such that the spray device is discarded after a single use. Such a configuration can reduce likelihood of contamination and can reduce or eliminate the burden of cleaning and reassemble parts of a spray instrument when a nozzle becomes clogged. In some circumstances, the spray device can contain predetermined volume of the viscous fluid so as to encourage the single-use operability.

Third, the spray device can be used to dispense an adhesive made of components that are premixed and stored in a reservoir of the spray device. As such, the spray device can promptly dispense the adhesive fluid without the requirement of mixing two reactive chemical components immediately before dispensation.

Fourth, the spray device can maintain a viscous fluid and a propellant fluid in isolation from each other until the fluids and have exited the nozzle. As such, the spray device can deliver the viscous fluid to the targeted site without having to premix the propellant fluid with the viscous fluid.

Fifth, because the spray device can deliver the viscous fluid to the targeted site without having to premix the propellant fluid with the viscous fluid, the propellant fluid does not dilute or degrade the viscous fluid stored inside the spray device. Such a configuration can be particularly useful when dispensing a sensitive adhesive (e.g., a moisture-sensitive adhesive or the like) that could suffer a loss of quality or usefulness if diluted or otherwise mixed with a propellant fluid prior to dispensation. Accordingly, the spray device can store the sensitive adhesive fluid or the like in the isolated condition for a period of up to 12 months.

Sixth, the spray device can have a self-contained configuration in which the supply of the viscous fluid and the supply of the propellant are stored and contained with the spray device housing. In particular, the propellant reservoir can contain the supply of the propellant fluid within the spray device housing so that the spray device can operate without requiring a connection to external gas supply equipment. Accordingly, the spray device can carry both the viscous fluid and the propellant fluid in a handheld and portable housing.

Seventh, the spray device can provide a single-button operation that causes the release of both the viscous fluid from its reservoir and the propellant fluid from its reservoir. As such, the single-button operation can be employed to dispense fluids from two separate reservoirs and arranged inside the spray device, thereby providing the user with an intuitive configuration that accommodates use even when wearing gloves.

Eighth, one or more spray devices can be part of a packaged system that permits the sprays devices to be readily available to a user in a safe and reliable manner. For example, the system can include a set of the spray devices arranged in a surgical storage module that fits within a surgical instrument rack arranged in an operating room. Accordingly, the surgical storage module (having the new spray devices contained therein) can be readily received from a supplier and then fit into the surgical instrument rack for immediate or subsequent use in a surgical environment. Such a configuration can reduce the burden of staff workers responsible for material handling and inventory restocking.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION OF ILLUSTRATIVE EMBODIMENTS

Figure 1:
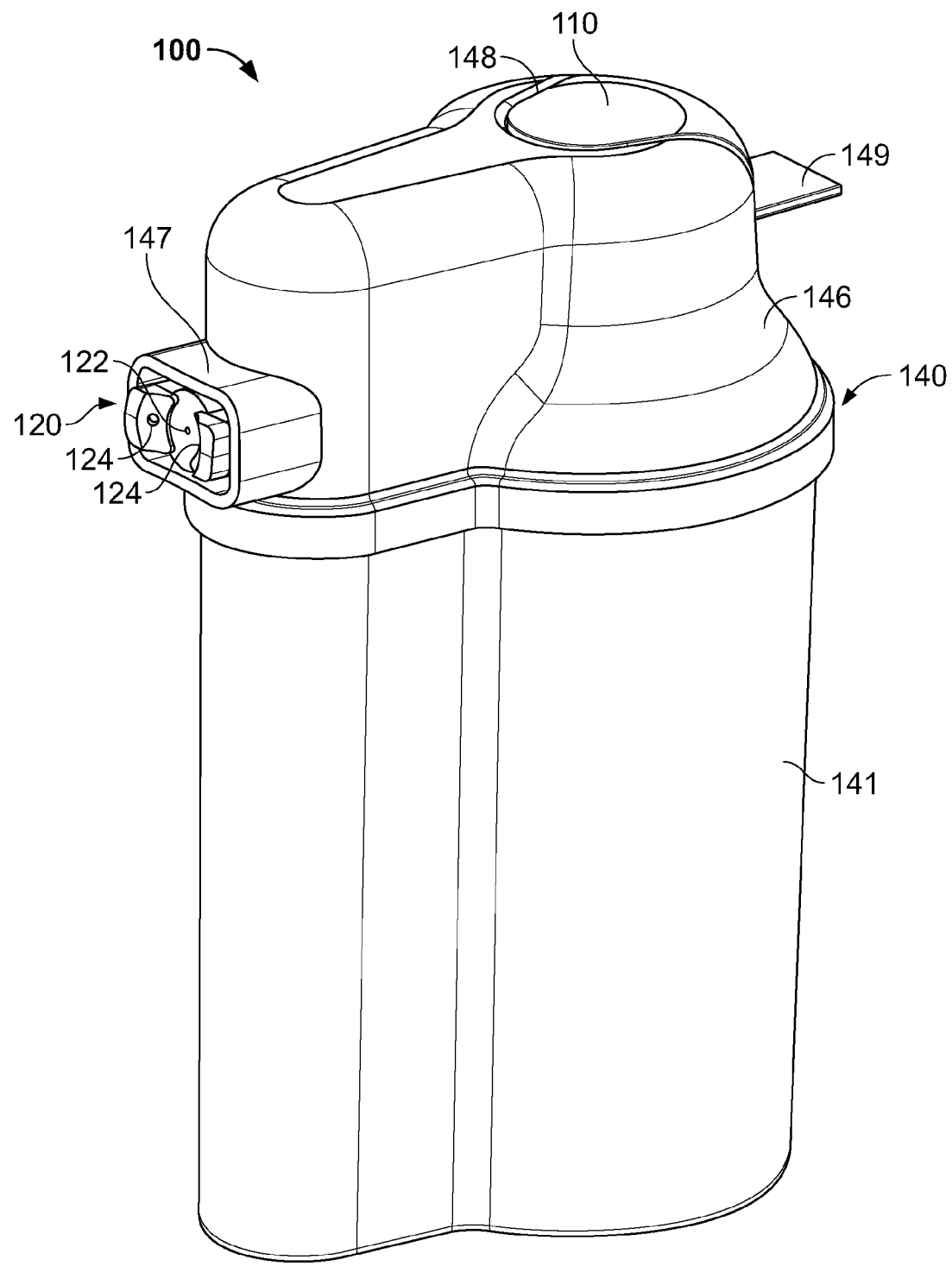
FIG. 1 is a perspective view of a spray device in accordance with some embodiments.
Figure 2:
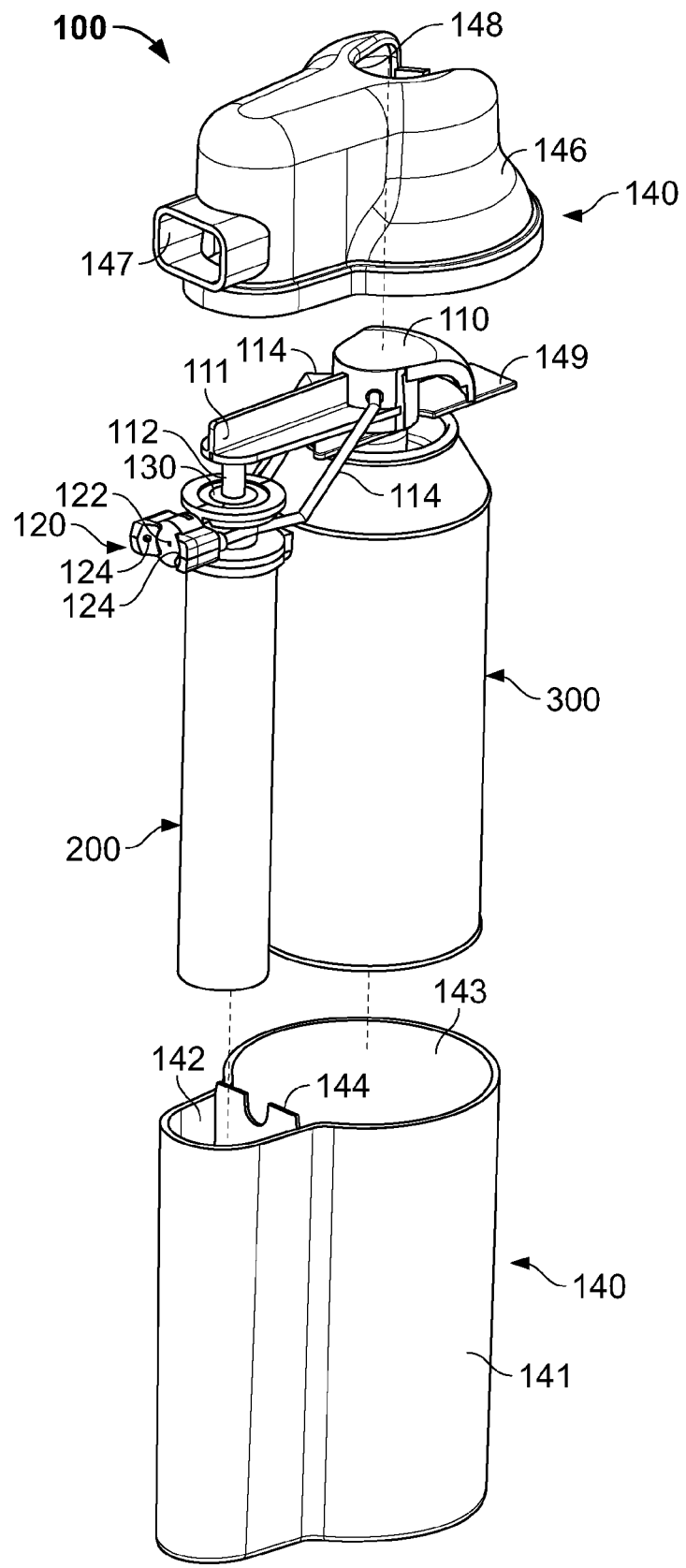
FIG. 2 is a perspective exploded view of the spray device of FIG. 1.
Figure 3:
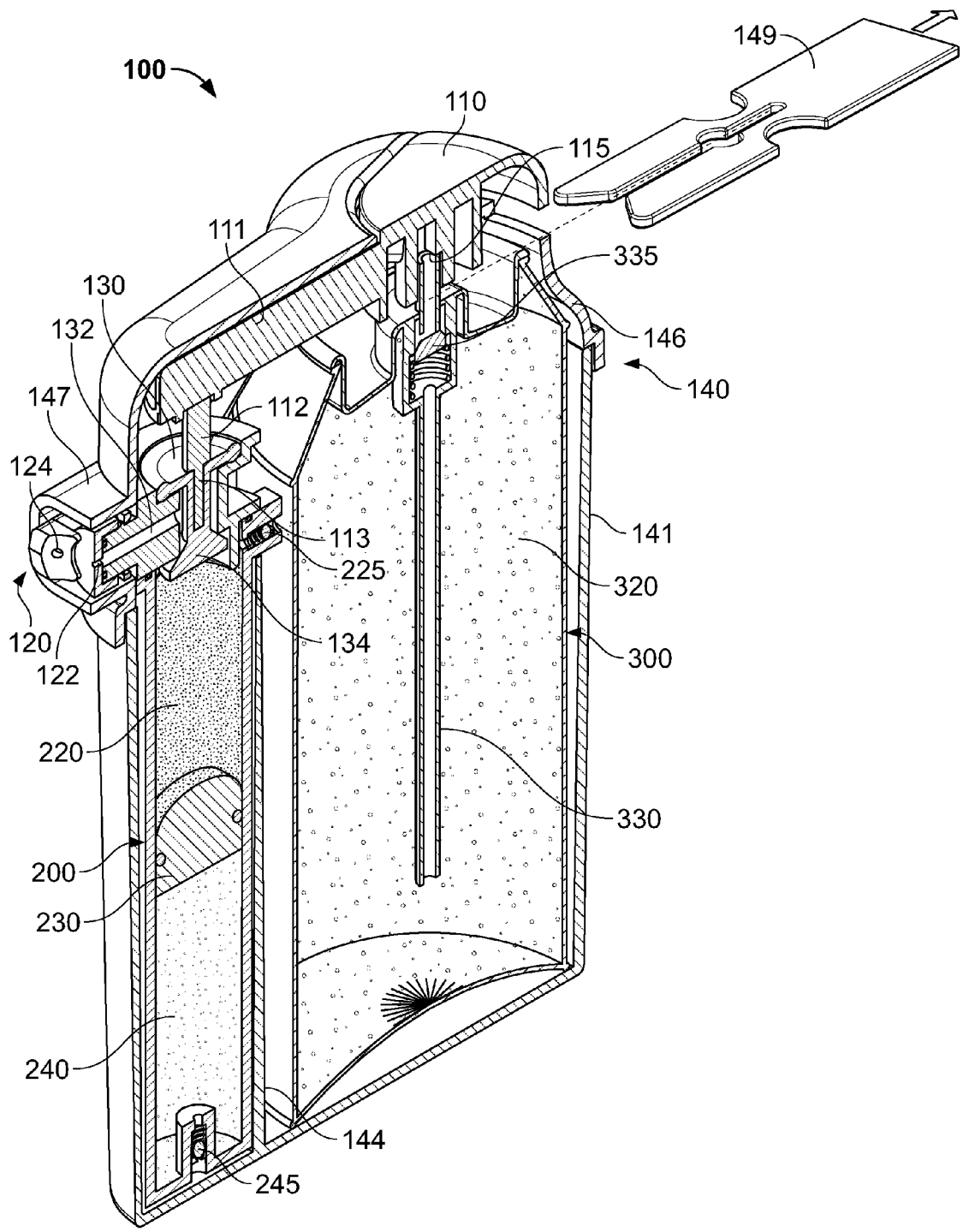
FIG. 3 is a cross-sectional view of the spray device of FIG. 1.

Referring to FIGS. 1-3, some embodiments of a spray device 100 can be configured to maintain a viscous fluid 220 (e.g., a surgical adhesive or the like) in isolation from a propellant fluid 320 until after the fluid 220 exits from a nozzle 120 of the spray device 100. As described in more detail below, the spray device 100 can be actuated by a user, thereby causing the viscous fluid 220 to exit a central port 122 of the nozzle 120 while the propellant fluid 320 exits from one or more side ports 124 of the nozzle 120. The propellant fluid 320 is dispensed from the side ports 124 such that it acts upon the exiting stream of viscous fluid 220 to break the stream into droplets that are deposited at a targeted site (described in more detail below in connection with FIGS. 4-6). As such, the spray device 100 can deliver the viscous fluid 220 from a reservoir 200 housed in the spray device 100 to the targeted site without having to premix the propellant fluid 320 with the viscous fluid 220.

In particular circumstances, the spray device 100 can be useful for dispensing adhesives having a relatively high viscosity, such as some surgical adhesives having viscosities from about 200 cP (centipoises) or greater, about 200 cP to about 2,000 cP, about 500 cP to about 1500 cP, and about 500 cP to about 700 cP (measured at 25° C.). For instance, the spray device 100 can isolate the propellant fluid 320 and release it from the side ports 124 with sufficient energy so as to break the adhesive 220 into droplets for spraying toward a targeted site. As described in more detail below, the propellant fluid 320 may comprise a propellant that is in a gaseous state at ambient air pressure, however, the propellant fluid 320 may be pressurized within the reservoir 300 so that it is stored at least partially in a liquid state. Because the supply of propellant fluid 320 is housed in the spray device 100, the adhesive 220 can be readily sprayed without requiring a hookup to separate gas supply equipment. In addition, the spray device 100 can be used to dispense an adhesive 220 (or other viscous fluid) without premixing the propellant with the adhesive 220 in the container. Such a configuration can be particularly useful when dispensing a sensitive adhesive (e.g., a moisture-sensitive adhesive or the like) that could suffer a loss of quality or usefulness if diluted or otherwise mixed with a propellant fluid 320 prior to dispensation.

Still referring to FIGS. 1-3, the spray device 100 can include a housing 140 to contain both the viscous fluid reservoir 200 and the propellant reservoir 300. In this embodiment, the housing 140 comprises a base 141 that mates with a lid 146 so as to at least partially define an interior space 142 to receive the viscous fluid reservoir 200 and an interior space 143 to receive the propellant reservoir 300. As shown in FIG. 2, the interior spaces 142 and 143 may be at least partially separated by a divider wall 144. Also in this embodiment, the lid 146 defines a shield 147 that provides access to the nozzle 120. The shield 147 can fit over an outer area of the nozzle 120 while permitting the nozzle ports 122 and 124 to be directed outwardly from the housing 140. The lid 146 may also include an actuator opening 148 that permits assembly of the actuator 110 with one or more components arranged in the housing 140. As described in more detail below in connection with FIG. 8, the actuator 110 may comprise a button that is pressed to an activated position by a user such that the actuator 110 moves relative to the lid 146. When the actuator 110 is in a non-activated position, the actuator 110 can fit with the actuator opening 148 in the lid 146.

In some embodiments, the spray device 100 can be equipped with a lock instrument 149 that reduces the likelihood of unintended dispensation of the viscous fluid 220. For example, the lock instrument 149 may comprise a removable tab 149 that releasably engages the actuator 110 (refer to FIGS. 2-3). The removable tab 149 can be positioned adjacent to the actuator 110 so as to prevent movement of the actuator 110 and any fluid dispensation resulting therefrom. When the spray device 100 is prepared for use, the removable tab 149 can be moved away from the actuator 110 (as shown in FIG. 3), thereby permitting the user to depress the actuator 110 and dispense fluid from the nozzle 120.

Referring to FIG. 2, the actuator 110 can be configured to cause the release of both the viscous fluid 220 from its reservoir 200 and the propellant fluid 320 from its reservoir 300. As such, a single-button operation can be employed to dispense fluids from two separate reservoirs 200 and 300 arranged inside the spray device 100, thereby providing the user with an intuitive configuration that accommodates use while wearing gloves (e.g., medical gloves worn by a surgeon or the like). As described in more detail below, the actuator 110 can be coupled with the propellant reservoir 300 such that, when the actuator 110 is depressed, the propellant fluid 320 to flows out of the reservoir 300, through one or more conduits 114, and toward the side ports 124 of the nozzle 120. In this embodiment, the actuator 110 is coupled to the viscous fluid reservoir 200 via an actuator arm 111 and a push rod 112. As described in more detail below, the actuator arm 111 and the push rod 112 move with the actuator 110 when the actuator 110 is depressed by the user, and the push rod 112 engages an adjustable valve 130 that controls the flow of the viscous fluid 220 from the reservoir 200. Accordingly, when the user presses upon the actuator 110, the push rod 112 acts upon the adjustable valve 130 to cause the release of the viscous fluid from the central port 122 of the nozzle 120.

Referring to FIG. 3, the adjustable valve 130 can control the release of the viscous fluid 220 by movement of a valve plug 134 that opens and closes the fluid path from the reservoir 200 to an output conduit 132. As previously described, the adjustable valve 130 is coupled to the push rod 112 of the actuator 110. For example, the push rod 112 may include a cylindrical extension 113 that mates with a complementary cavity in the valve 130. As described below in connection with FIGS. 7-8, when the push rod 112 is urged against the valve 130 (e.g., by the user depressing the actuator 110), the valve 130 flexes so that the valve plug 134 shifts to an open position, thereby permitting the viscous fluid 220 to pass into the output channel 132 and out of the central port 122 of the nozzle 120.

The viscous fluid 220 may be stored under pressure in the reservoir 200 so that the fluid 220 is urged to pass by the valve plug 134 when it is opened. In such circumstances, the viscous fluid reservoir 200 can include a bias instrument that causes the viscous fluid 220 to be stored under pressure. In the embodiment depicted in FIG. 3, the bias instrument comprises a pressurized gas 240 that is separated from the viscous fluid 220 by a movable plunger 230. For example, the pressurized gas 240 may comprise compressed air, compressed nitrogen gas, or the like. The pressurized gas 240 can be arranged in the reservoir 200 so as to serve as a gas spring the urges the plunger 230 against the viscous fluid 220. The movable plunger 230 can include an o-ring or other circumferential seal that inhibits the migration of the pressurized gas 240 toward the viscous fluid 220. In some embodiments, the pressurized gas 240 can be arranged in the reservoir 200, yet isolated from the viscous fluid 220, so as to cause the viscous fluid 220 to be stored under pressure at about 15 psi to about 40 psi, about 20 psi to about 30 psi, and about 20 psi in this embodiment. Because the viscous fluid 220 is stored generally at a pressure greater than the ambient air pressure, the viscous fluid 220 is urged to flow pass the valve plug 134 when it is shifted to the open position (described below in connection with FIG. 8).

Still referring to FIG. 3, the viscous fluid reservoir 200 can include a fill port 225 that permits the viscous fluid 220 to be promptly and safely deposited in the reservoir during manufacture. In this embodiment, the fill port 225 is in fluid communication with the internal space of the reservoir 200 on the wet side of the plunger 230. The fill port 225 can include a check valve configuration that permits the viscous fluid to pass into the internal space, but inhibits reverse flow out through the fill port 225. In the embodiments in which the bias instrument comprises the pressurized gas 240, the reservoir 200 can include a second fill port 245 for depositing the pressurized gas 240. In this embodiment, the fill port 245 is in fluid communication with the internal space of the reservoir 200 on the drive side of the plunger 230. The fill port 245 can also include a check valve configuration that permits the pressurized to pass into the internal space, but inhibits reverse flow out through the fill port 225.

As shown in FIG. 3, the propellant reservoir 300 can contain a supply of the propellant fluid 320 within the housing 140 so that the spray device 100 can operate without requiring a connection to external gas supply equipment. Accordingly, the spray device 100 can provide a self-contained configuration in that the spray device 100 houses both the viscous fluid 220 and the propellant fluid 320 in handheld and portable housing 140. The propellant fluid 320 may comprise a propellant that can be stored at least partially in a liquid state within the reservoir 300 and then expands upon release to create a gas-like mist of propellant particles. A suitable propellant fluid can include a hydrofluorocarbon (HFC) propellant. For example, the propellant fluid may comprise a Dupont™ Dymel® propellant such as Dymel® HFC 134a or Dymel® HFC 227ea. Accordingly, the propellant fluid 320 may comprise a propellant that is in a gaseous state at ambient air pressure, however, the propellant fluid 320 may be pressurized within the reservoir 300 so that it is stored at least partially in a liquid state.

The propellant reservoir 300 can include an internal conduit 330 that leads to release valve 335. The release valve 335 can be used to control the flow of the propellant fluid 320 from the reservoir 300, through the output conduits 114 (FIG. 2), and out of the nozzle 120. As described in more detail below in connection with FIGS. 7-8, the actuator 110 can act upon the release valve 335 so that the user can selectively control the release of the propellant fluid 320. For example, the actuator 110 may define a shoulder 115 that engages a component of the release valve 335 so as to control the release of the propellant fluid 320.

Accordingly, the actuator 110 can be shifted by the user so as to contemporaneously release the viscous fluid 220 from its reservoir 200 and the propellant fluid 320 from its reservoir 300. The spray device 100 can maintain the viscous fluid 220 and the propellant fluid 320 in isolation from each other until the fluids 220 and 320 have exited the nozzle ports 122 and 124, respectively. As such, the spray device 100 can deliver the viscous fluid 220 to the targeted site without having to premix the propellant fluid 320 with the viscous fluid 220. Such a configuration can be particularly useful when dispensing a sensitive adhesive (e.g., a moisture-sensitive adhesive or the like) that could suffer a loss of quality or usefulness if diluted or otherwise mixed with a propellant fluid prior to dispensation.

Figure 4:
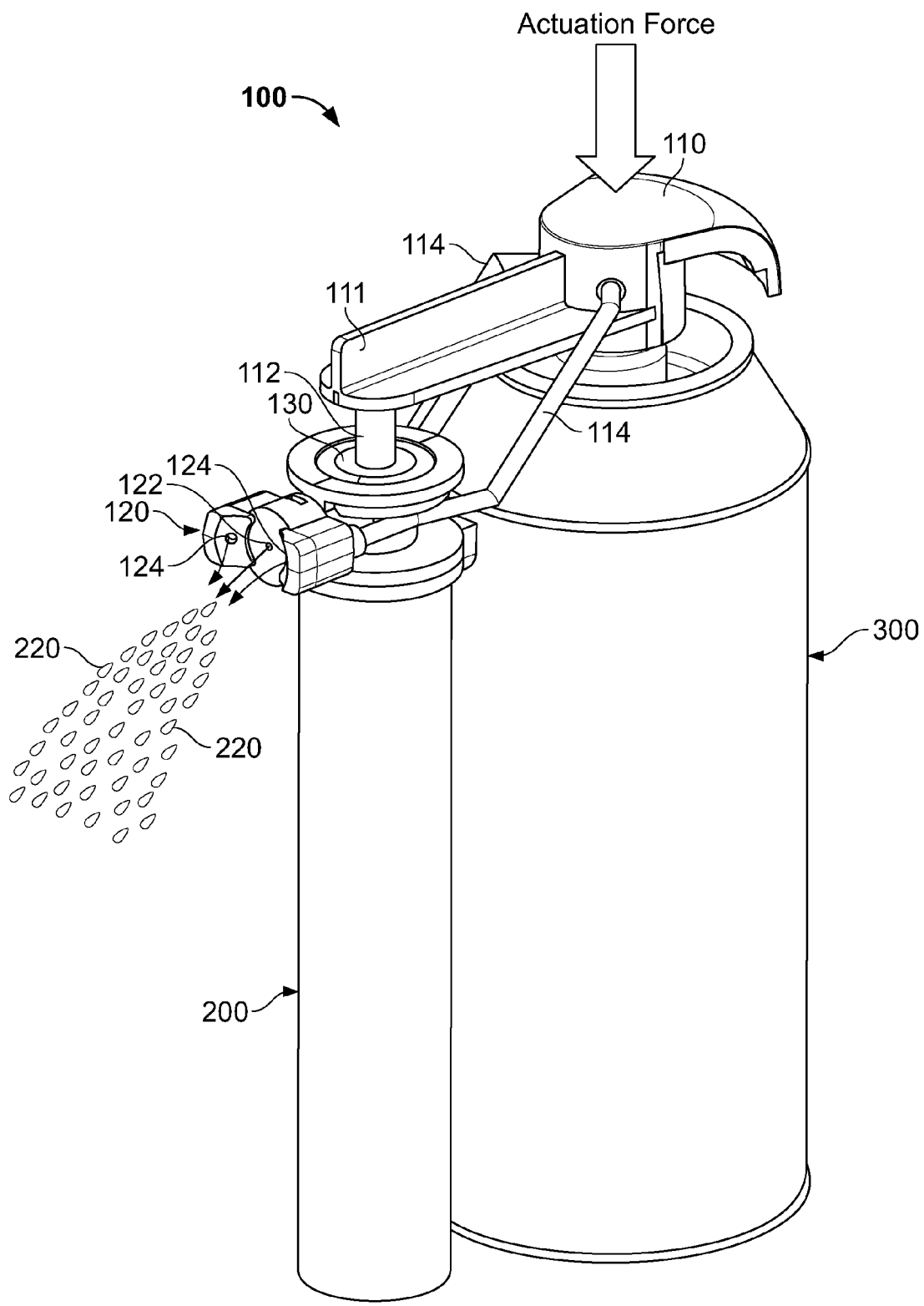
FIG. 4 is a perspective view of a portion of the spray device of FIG. 1.
Figure 5:
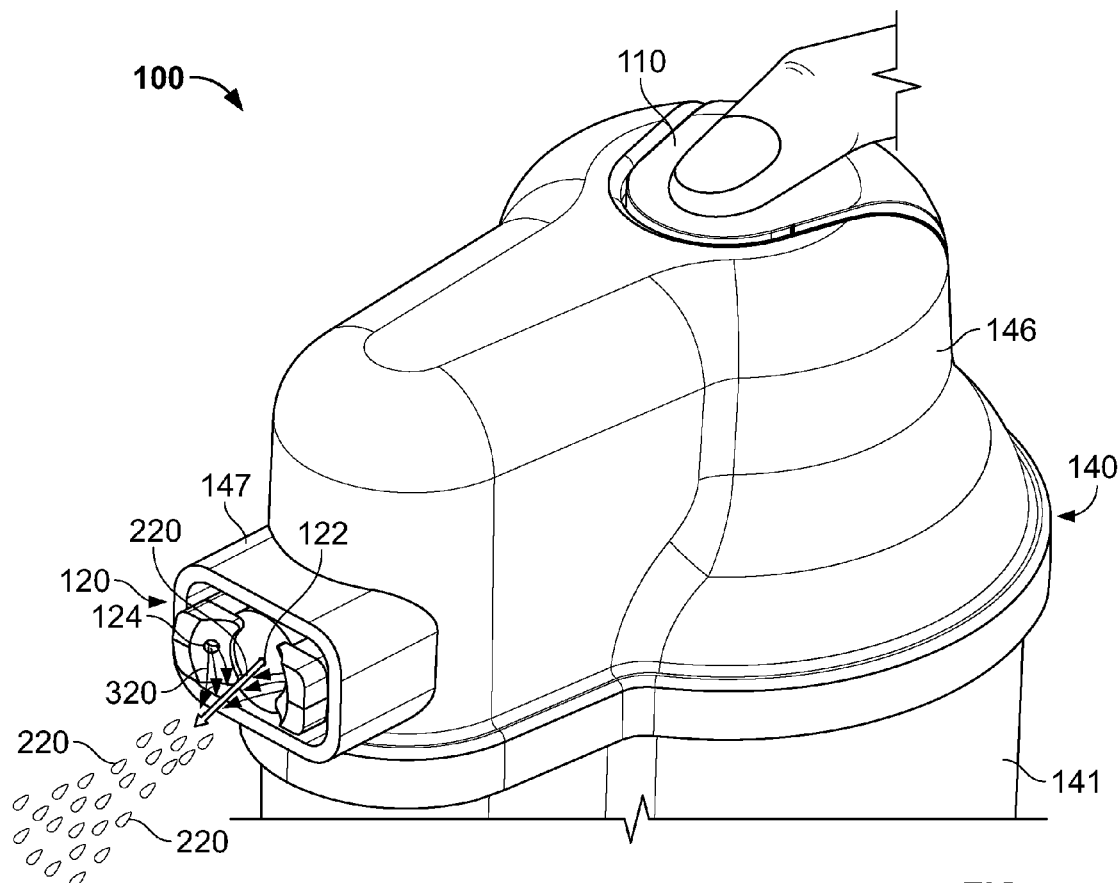
FIG. 5 is a perspective view of a spray device dispensing droplets of a surgical adhesive in accordance with some embodiments.
Figure 6:
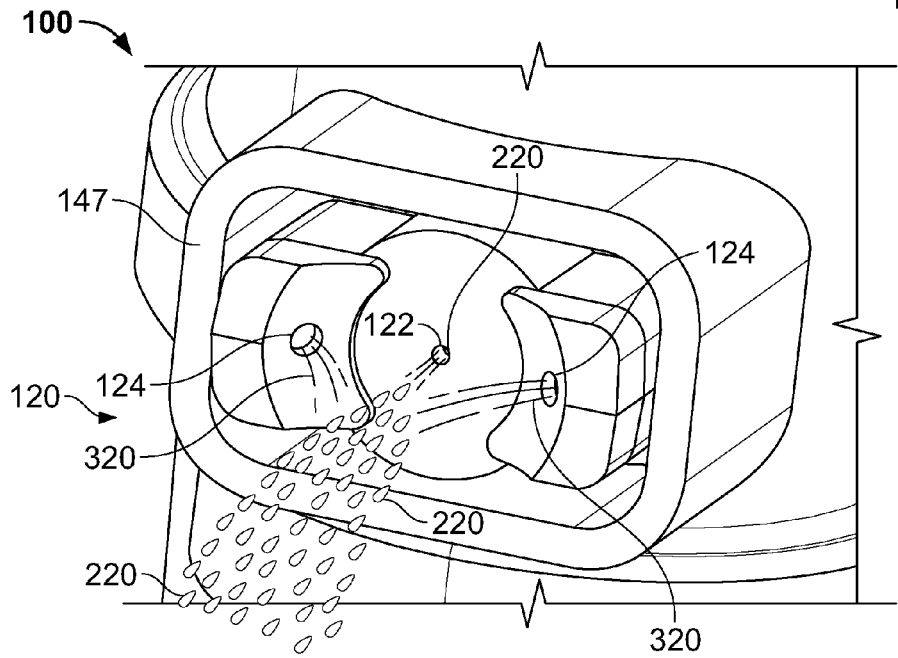
FIG. 6 is an enlarge perspective view of the spray device of FIG. 5.

Referring now to FIGS. 4-6, the nozzle of the spray device 120 is configured to output the viscous fluid 220 and the propellant fluid 320 in a manner that causes the propellant fluid 320 to act upon the exiting stream of viscous fluid 220, thereby breaking the stream into droplets. The user can readily apply an actuation force to the actuator 110 while directing the nozzle 120 so that the droplets of the viscous fluid 220 are delivered toward a targeted site. In one example, the viscous fluid 220 may comprise a surgical adhesive that is used to close incisions, wounds, or other openings in a patient's skin. Because the surgical adhesive 220 may be moisture sensitive or may degrade in quality if premixed with a propellant before dispensation, the spray device 100 isolates the surgical adhesive 220 from the propellant fluid 320. Upon dispensation, the propellant fluid 320 acts upon the exiting stream of surgical adhesive 220 to break the stream into droplets of adhesive. In such circumstances, the surgical adhesive droplets can be delivered to a targeted tissue site for purposes of closing an incision, a wound, or the like.

As shown in FIG. 4, the user can apply an actuation force to the actuator 110. For example, the user may grasp the spray device housing 140 (not shown in FIG. 4 for purposes of viewing internal components) and press the actuator 110 with his or her finger. Upon actuation, the propellant fluid 320 is released from the reservoir 300, flows through the propellant conduits 114, and exits out of the nozzle ports 124. Also upon actuation, the viscous fluid 220 is released from its reservoir 200, flows pass the plug of the adjustable valve 130, and exits out of the nozzle port 122.

Referring to FIG. 5, when the user moves the actuator 110 with his or her finger, the nozzle 120 outputs both the viscous fluid 220 and the propellant fluid 320. (The user's gloves are removed from view in FIG. 5 for purposes of illustrating the finger.) As previously described, the viscous fluid 220 may initially exit the central nozzle port 122 in a formation that is not separated into droplets. Immediately after the viscous fluid 220 exits the port 122, the propellant gas 320 exiting the side ports 124 can commingle with the viscous fluid stream to thereby break the viscous fluid 220 generally into droplet formations. For example, the droplet formations of the viscous fluid 220 may have an average droplet size of about 0.5 mm to about 3.0 mm, depending upon the viscosity of the fluid 220, the energy of the propellant gas exiting the ports 124, and other factors.

Referring to closer view depicted in FIG. 6, the propellant ports 124 of the nozzle 120 may be directed toward one or more of the viscous fluid ports 122. In this embodiment, the propellant ports 124 comprise side ports 124 that are angularly oriented toward the central port 122 that dispenses the viscous fluid 220. Thus, the propellant ports 124 are oriented to be non-parallel with each other and oriented to be non-parallel with the central port 122. In such circumstances, the propellant fluid 320 exiting the side ports 124 can be directed toward the viscous fluid 220 that is exiting the central port 122. As previously described, the propellant fluid 320 may exit the side ports 124 in a gas-like mist of propellant particles, which can interact with the stream of viscous fluid 220 exiting the central port 122. In particular, the propellant fluid 320 can act upon the exiting stream of viscous fluid 220 to generate droplet formations of the viscous fluid 220. After the viscous fluid 220 is broken into droplet formations, the viscous fluid continues in general direction to the targeted site, whereupon the droplet formations can coat the targeted site with the viscous fluid 220.

Figure 7:
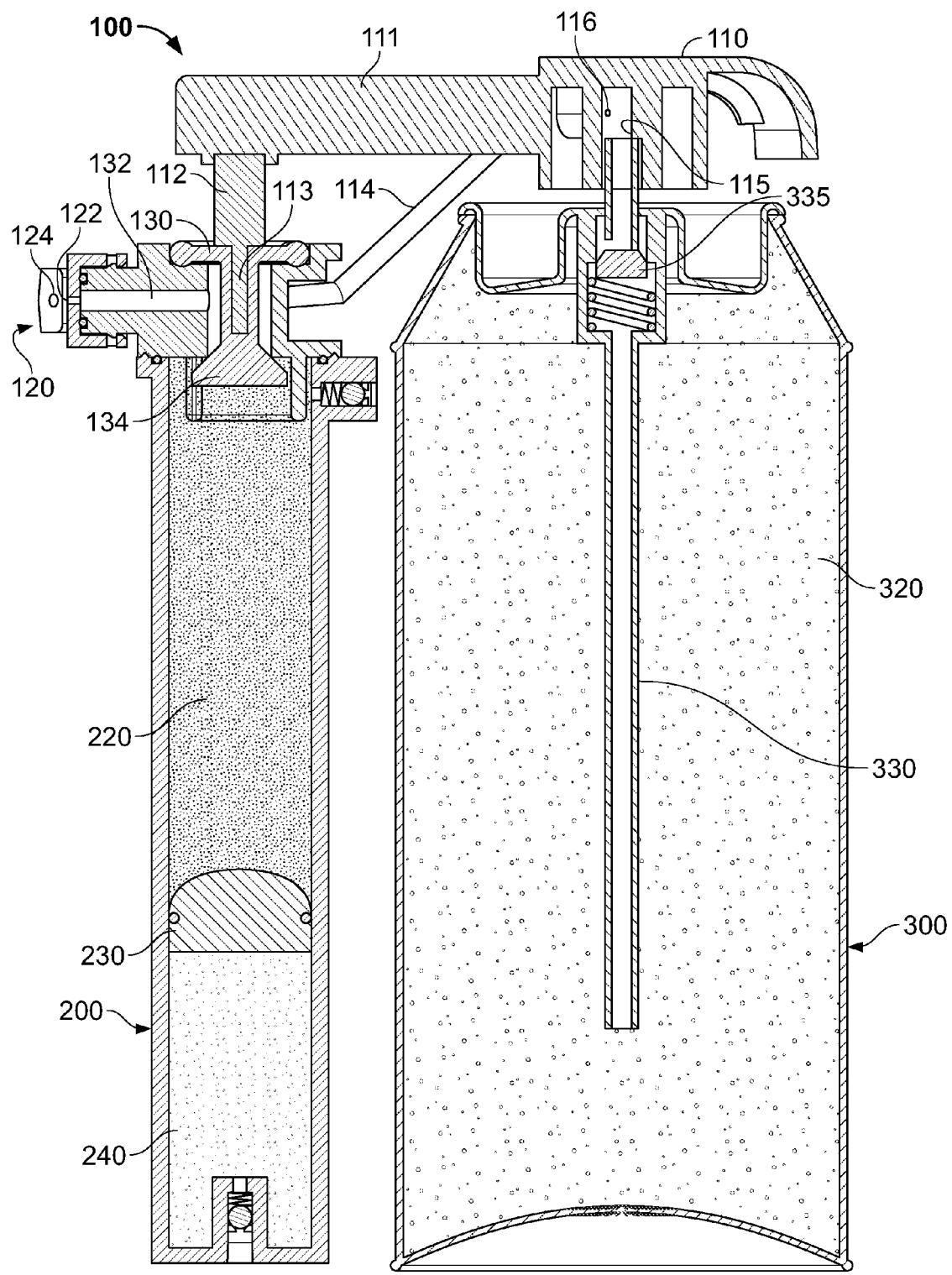
FIG. 7 is a cross-sectional view of a spray device with an actuator in a first position, in accordance with some embodiments.
Figure 8:
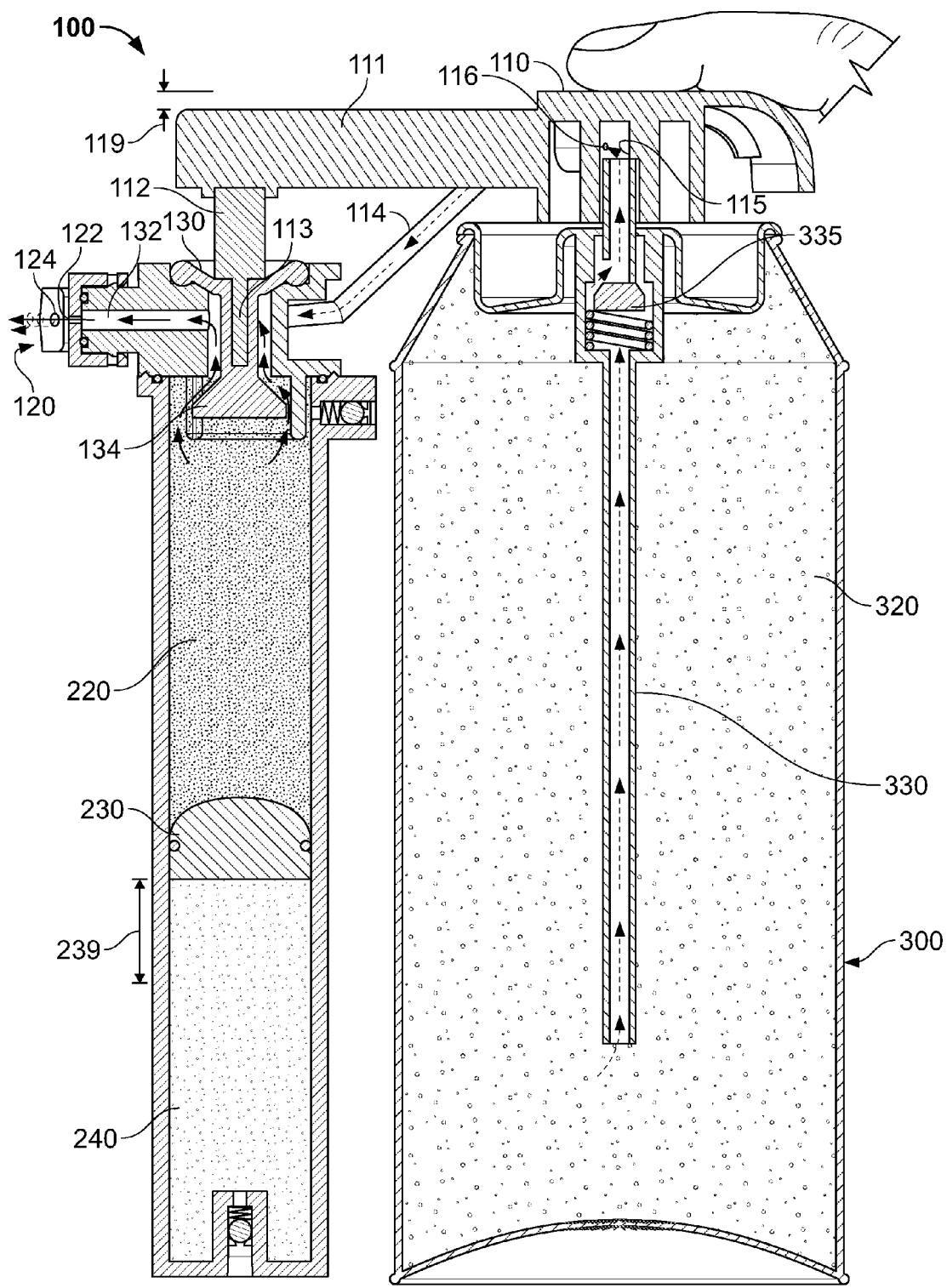
FIG. 8 is a cross-sectional view of the spray device of FIG. 7 with the actuator in a second position.

Referring now to FIGS. 7-8, the operation of the actuator 110 can be used to contemporaneously release the viscous fluid 220 and the propellant fluid 320 from their respective reservoirs 200 and 300. As shown in FIG. 7, the actuator 110 is in a non-activated position, and the viscous fluid 220 and the propellant fluid 320 are retained in their respective reservoirs 200 and 300. As shown in FIG. 8, the actuator 110 is shifted to an activated position by depressing the actuator 110 to cause a movement 119. When the actuator 110 is in the activated position, the viscous fluid 220 flows out of its reservoir 200 (the viscous fluid flow is represented with solid arrow lines in FIG. 8), through the output conduit 132, and out of the central port 122. Contemporaneously, the propellant fluid 320 flows out of its reservoir 300 (the propellant fluid flow is represented with dotted arrow lines in FIG. 8), through the propellant conduits 114, and out of the side ports 124.

As previously described, the adjustable valve 130 can control the release of the viscous fluid 220 by movement of the valve plug 134 that opens and closes the fluid path from the reservoir 200 to the output conduit 132. Because the adjustable valve 130 is coupled to the push rod 112 of the actuator 110, the adjustable valve 130 shifts in response to movement of the actuator 110. In this embodiment, the adjustable valve 130 comprises a flexible polymer material that bends when the when the push rod 112 is urged against the valve 130 (e.g., by the user depressing the actuator 110 as shown in FIG. 8). The valve 130 flexes so that the valve plug 134 shifts to an open position, thereby permitting the viscous fluid 220 to pass into the output channel 132 and out of the central port 122 of the nozzle 120.

Still referring to FIGS. 7-8, the viscous fluid 220 is retained in its reservoir 200 stored under pressure so that the fluid 220 is urged to pass by the valve plug 134 when it is opened. As previously described, the viscous fluid reservoir 200 can include a bias instrument that causes the viscous fluid 220 to be stored under pressure. For example, the bias instrument comprises the pressurized gas 240 that is separated from the viscous fluid 220 by a movable plunger 230, thereby permitting the pressurized gas 240 to serve as a gas spring the urges the plunger 230 against the viscous fluid 220. Because the viscous fluid 220 is stored generally at a pressure greater than the ambient air pressure, the viscous fluid 220 is urged to flow pass the valve plug 134 when it is shifted to the open position.

When the viscous fluid 220 flows out of the reservoir 200, the movable plunger 230 may shift positions due to the pressure applied by the pressurized gas 240. For example, as shown in FIG. 8, the movable plunger 230 slides upwardly in a movement 239 toward the valve 130 as the viscous fluid 220 is dispensed from the spray device 100. The plunger 230 may comprise a polymer material that slidably engages the interior wall of the reservoir 200. In such circumstances, the pressurized gas 240 can apply a pressure that drives the plunger 230 toward the valve 230 when some or all of the viscous fluid 220 is released through the valve 130.

In some embodiments, the viscous fluid reservoir 200 may be filled with only a limited amount of the viscous fluid 220 sufficient for a single use. For example, the spray device 100 may house a selected amount of surgical adhesive 220 or other viscous fluid that is predetermined to provide a generally continuous spray of adhesive droplets for a period of about 3 seconds to about 15 seconds, about 5 seconds to about 10 seconds, and about 5 seconds in this embodiment. After the surgical adhesive 220 is exhausted from its reservoir 200, the entire spray device 100 can be conveniently discarded (as described, for example, in connection with FIGS. 14-17).

Still referring to FIGS. 7-8, the spray device 100 can contain the supply of the propellant fluid 320 within the housing 140, and thereby operates as a handheld portable instrument that does not require a connection to external gas supply equipment. In the embodiment depicted in FIG. 8, the propellant reservoir 300 includes the internal conduit 330 which leads to the release valve 335. The release valve 335 controls the flow of the propellant fluid 320 from the reservoir 300. For example, the release valve 335 shifts to an open position (FIG. 8) in response to the movement 119 the actuator 110 so that the user can selectively control the release of the propellant fluid 320. In this embodiment, the actuator 110 includes the shoulder 115 that engages a component of the release valve 335 to trigger the flow of the propellant fluid 320 from its reservoir 300, pass the release valve 335, through internal ports 116 to the conduits 114, and out of the nozzle ports 124.

Thus, as shown in FIG. 8, the actuator 110 can be shifted by the user so as to contemporaneously release the viscous fluid 220 to flow from its reservoir 200 and the propellant fluid 320 from its reservoir 300. The spray device 100 can maintain the viscous fluid 220 and the propellant fluid 320 in isolation from each other until the fluids 220 and 320 have exited the nozzle ports 122 and 124, respectively.

Figure 10:
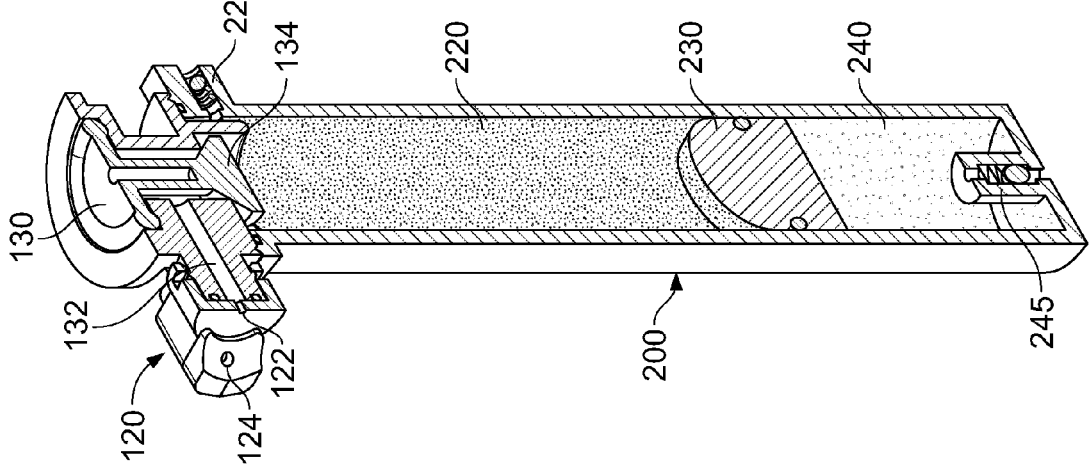
FIG. 10 is a cross-sectional view of the surgical adhesive container of FIG. 9, in accordance with some embodiments.
Figure 9:
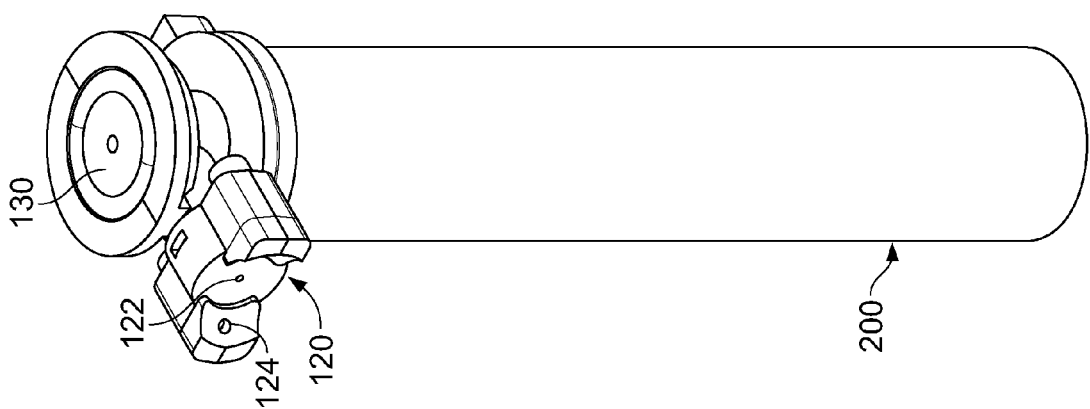
FIG. 9 is a perspective view of a surgical adhesive container for a spray device.

Referring now to FIGS. 9-10, the viscous fluid reservoir 200 can be assembled with the nozzle 120 and the adjustable valve 130 to provide a sealed container for the viscous fluid 220. Optionally, this sealed container can be separately stored prior to assembly into the spray device housing 140 (FIGS. 1-3) for final manufacture. In such circumstances, the viscous fluid reservoir 200 (assembled with the nozzle 120 and the valve 130) can operate as a cartridge that is inserted into the interior space 142 of the housing 140 during manufacture. In the embodiments in which the viscous fluid 220 is a surgical adhesive or other fluid that will be applied in a medical procedure, the cartridge depicted in FIGS. 9-10 can be stored in a controlled environment and can be separately sterilized prior to the final manufacture of the spray device 100 (FIGS. 1-3).

As shown in FIG. 10, the viscous fluid 220 is retained in the reservoir 200 under pressure due to the pressurized gas 240 that is separated from the viscous fluid 220 by the movable plunger 230. The pressurized gas 240 can comprise compressed air, compressed nitrogen gas, or the like so that the pressurized gas 240 serves as a gas spring that urges the plunger 230 against the viscous fluid 220. As previously described, the viscous fluid 220 can be retained in the reservoir 200 under pressure at about 15 psi to about 40 psi, about 20 psi to about 30 psi, and about 20 psi in this embodiment. Because the viscous fluid 220 is stored generally at a pressure greater than the ambient air pressure, the viscous fluid 220 forces the valve plug 134 to a sealed position when the valve 130 is not assembled with the actuator 110.

Still referring to FIG. 10, the fill port 225 can be connected to a viscous fluid supply line (not shown in FIG. 10) during manufacture so that the viscous fluid 220 can be promptly and safely deposited in the reservoir 200 during manufacture. In some embodiments, the fill port 225 can include a check valve that permits the viscous fluid 220 to pass into the internal space on the wet side of the plunger 230, but inhibits reverse flow out through the fill port 225. The second fill port 245 can be used to deposit the pressurized gas 240 in the internal space opposite to the viscous fluid 220. Similar to the first fill port 225, the second fill port 245 can include a check valve that permits the pressurized gas 220 to pass into the reservoir 200 while inhibiting reverse flow out of the reservoir 200.

Figure 11:
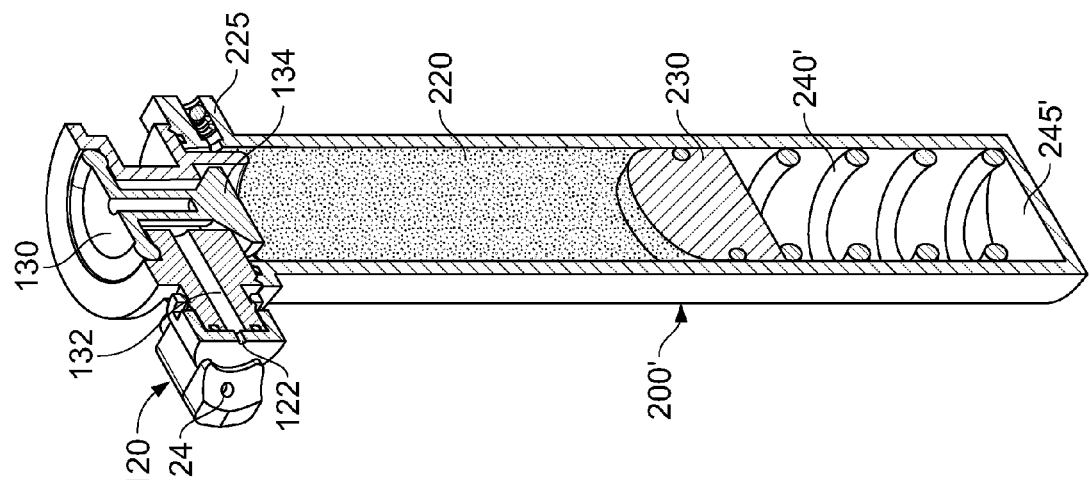
FIG. 11 is a cross-sectional view of a surgical adhesive container in accordance with other embodiments.

Referring now to FIG. 11, it should be understood from the description herein that the viscous fluid reservoir is not limited to the embodiments described in FIGS. 1-10. Rather, the reservoir may have other configurations that provide for the dispensation of the viscous fluid 220 out of the nozzle 120. For example, in the embodiment depicted in FIG. 11, an alternative embodiment of the viscous fluid reservoir 200' may include a bias instrument other than the pressurized gas 240 (FIG. 10). In this embodiment, the bias instrument comprises a spring device 240' that urges the movable plunger 230 against the viscous fluid 220. As such, the spring device 240' applies a force to the movable plunger 230 that causes the viscous fluid 220 to be maintained under pressure. The movable plunger 230 can include an o-ring or other circumferential seal that inhibits the migration of the viscous fluid 220 toward the spring device 240'. The spring device 240' can be a mechanical spring that is selected to provide a force that causes the viscous fluid 220 to be retained in the reservoir 200 under pressure at about 15 psi to about 40 psi, and about 20 psi to about 30 psi in this embodiment. In these circumstances, the reservoir 200' can include a surface 245' that engages the spring device 240' opposite the plunger 230.

Figure 12:
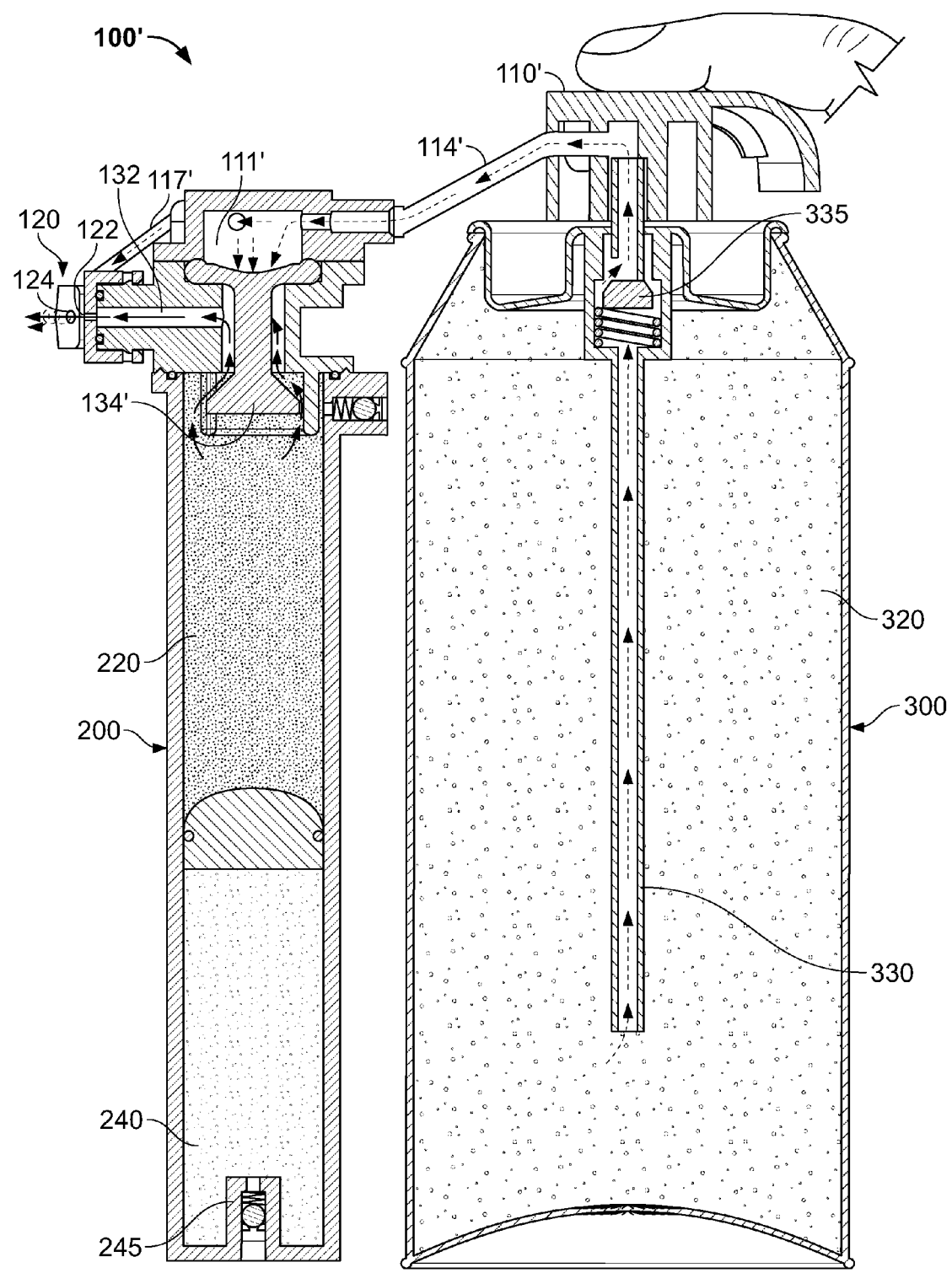
FIG. 12 is a cross-sectional view of a portion of a spray device in accordance with other embodiments.

Referring now to FIG. 12, some embodiments of the spray device can provide alternative techniques to actuate the release of the viscous fluid 220. For example, in the depicted embodiment, the spray device 100' uses the pressure from the propellant fluid 320 to actuate the adjustable valve 130'. In such circumstances, the viscous fluid 220 is not released from its reservoir 200 until the propellant fluid 320 has begun to flow, thereby reducing the likelihood that the viscous fluid 220 would be dispensed from the nozzle 120 without the propellant fluid 320.

Similar to previously described embodiments, the operation of the actuator 110' can be used to release both the viscous fluid 220 and the propellant fluid 320 from their respective reservoirs 200 and 300. In this embodiment, when the actuator 110' is shifted to an activated position by depressing the actuator 110'(e.g., with the user's finger), the propellant fluid 320 flows out of its reservoir 300 (the propellant fluid flow is represented with dotted arrow lines in FIG. 12), through a propellant conduit 114', and into a pressure chamber 111' adjacent to the adjustable valve 130'. The propellant fluid 320 in the pressure chamber 111' acts upon a surface of the adjustable valve 130' to force the valve plug 134' to an opened position. Also, the propellant fluid 320 in the pressure chamber 111' can pass through one or more secondary conduits 117' to the nozzle 120 for dispensation out of corresponding side ports 124.

Still referring to FIG. 12, when the propellant fluid 320 in the pressure chamber 111' acts upon the valve 130' to move the plug 134' to the opened position, the viscous fluid 220 flows out of its reservoir 200 (the viscous fluid flow is represented with solid arrow lines in FIG. 12), through the output conduit 132, and out of the central port 122. Accordingly, the adjustable valve 130' shifts in response to movement of the actuator 110 to release the viscous fluid 220 even though the valve 130' is not directly mounted to the actuator 110 (e.g., via a pushrod 112 shown in FIG. 8). In this embodiment, the adjustable valve 130' comprises a polymer material that flexes when the when the propellant fluid 320 in the pressure chamber 111' generates a force against the valve 130'. When the valve 130' flexes as described, the valve plug 134' shifts to the open position, thereby permitting the viscous fluid 220 to pass into the output channel 132 and out of the central port 122 of the nozzle 120.

Similar to previously described embodiments, the spray device 100' may be equipped to contain only a limited amount of the viscous fluid 220 sufficient for a single use. For example, the spray device 100' may house a selected amount of surgical adhesive 220 or other viscous fluid that is predetermined to provide a generally continuous spray of adhesive droplets for a period of about 3 seconds to about 15 seconds, about 5 seconds to about 10 seconds, and about 5 seconds in this embodiment. After the surgical adhesive 220 is exhausted from its reservoir 200, the entire spray device 100' can be conveniently discarded (as described, for example, in connection with FIGS. 14-17). Also, the spray device 100' can contain the supply of the propellant fluid 320 within the housing 140, which permits the spray device 100' to operate as a handheld portable instrument that does not require a connection to external gas supply equipment. Similar to previously described embodiments, the spray device 100' can maintain the viscous fluid 220 and the propellant fluid 320 in isolation from each other until the fluids 220 and 320 have exited the nozzle ports 122 and 124, respectively.

Figure 13:
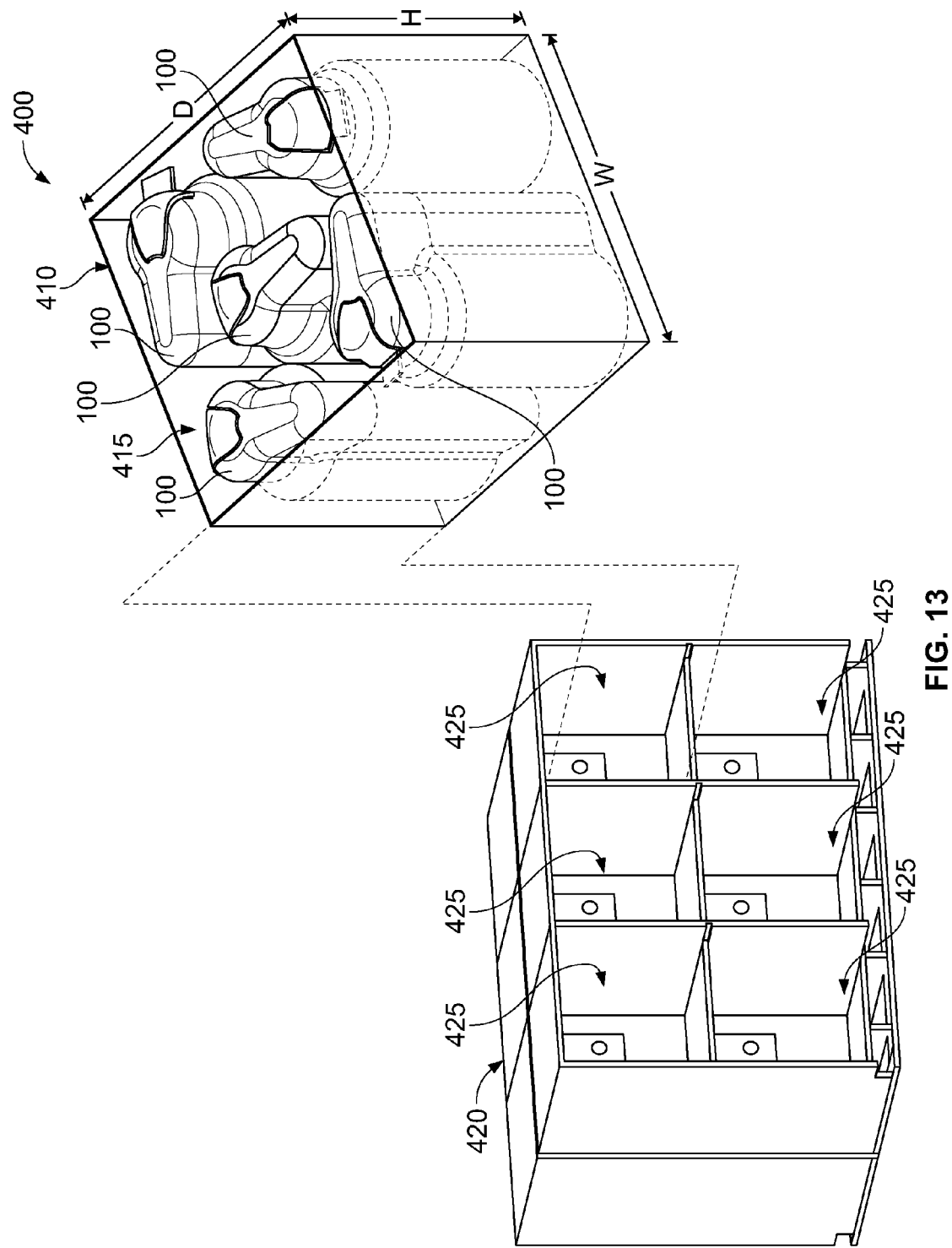
FIG. 13 is perspective view of a plurality of spray devices arranged in a surgical storage module, in accordance with some embodiments.

Referring now to FIG. 13, some embodiments of the spray device 100 may be configured for use in a medical procedure. As such, one or more spray devices 100 can be part of a packaged system 400 that permits the spray devices 100 to be readily available to the surgeon or other practitioner in a safe and reliable manner. For example, the system 400 can include a number of the spray devices 100 (e.g., about two to about ten, about three to about six, and about four to about five in this embodiments) arranged in an interior space 415 of a surgical storage unit 410. The surgical storage unit 410 may include a predetermined height H, width W, and depth D so as to fit within a cavity 425 of a surgical instrument rack 420 arranged in an operating room or the like. In some embodiments, each of the spray devices 100 in the module 410 can be separately wrapped and sterilized (e.g., in a sealed pouch which is not shown in FIG. 13 for purposes of illustrating the spray devices 100). Accordingly, the surgical storage module 410 (having the new spray devices 100 contained therein) can be readily received from a supplier and then fit into the surgical instrument rack 425 for immediate or subsequent use in a surgical environment. Such a configuration can reduce the burden of staff workers responsible for material handling and inventory restocking.

In this particular embodiment, the surgical storage module 410 is sized to receive five spray devices 100 in the interior space 415. As shown in FIG. 13, the spray devices 100 can be stored in their upright positions so as to reduce the likelihood of dislodging the locking tab 149 or activating the spray device actuator 110 during transport. An exemplary method of manufacturing and packaging the spray devices 100 is described in more detail below in connection with FIG. 18. Each of the spray devices 100 may have an overall height of about 14 cm or less, about 13.5 cm or less, about 10 cm to about 13 cm, and about 12.7 cm in this embodiment. Also, each of the spray devices 100 may have a maximum width of about 9 cm or less, about 8.5 cm or less, about 5 cm to about 8 cm, and about 7.6 cm in this embodiment. As such, the set of five spray devices 100 can be packaged into the interior space of 415 the surgical storage module 410 having a height H of about 14 cm, a width W of about 12.5 cm, and a depth D of about 14 cm. The surgical storage module 410 is sized to fit within at least one of a plurality of cavities 425 in the surgical instrument rack 420. In this embodiment, the rack 420 includes six cavities 425. In other embodiments, the surgical instrument rack 420 can have other configurations suitable for use in an operating room or other medical environment.

Still referring to FIG. 13, some embodiments of the system 400 can include spray devices 100 that have a storage life of about 6 months to about 18 months, and about 12 months in this embodiment. For example, the components of the viscous fluid 220 can be combined and stored in the viscous fluid reservoir 200 (FIG. 3) in each spray device 100. After the spray devices 100 are manufactured and packaged into the surgical storage module 410, the spray devices 100 can be used by medical practitioners over a period of time, such days, weeks, or months. In some circumstances, the spray devices 100, the surgical storage module 410, or both may be labeled with an expiration date so as to notify the practitioner of the estimated useful life of each spray device.

Figure 14:
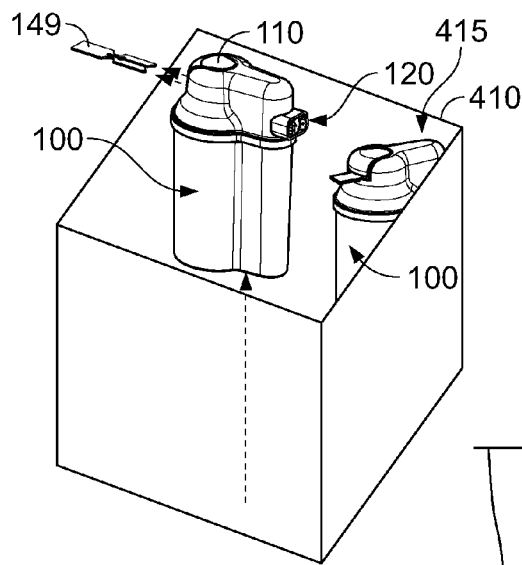
FIGS. 14-16 are perspective views of a disposable spray device that is discarded after a single use, in accordance with some embodiments.
Figure 15:
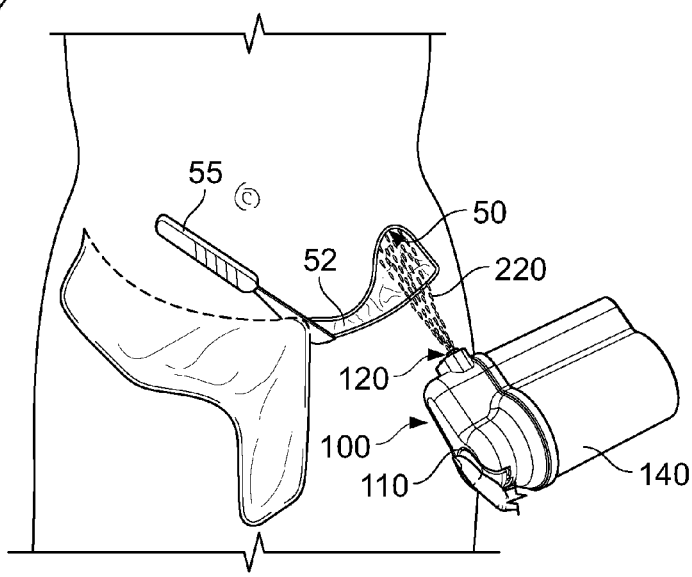
Figure 16:
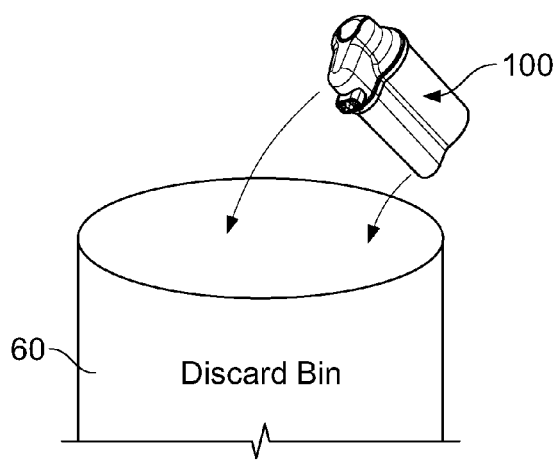

Referring now to FIGS. 14-16, some embodiments of the spray device 100 can be configured to dispense a viscous fluid 220 in the form of an adhesive. For example, the viscous fluid 220 can comprise a surgical adhesive that is spray onto a targeted tissue site for purposes of at partially closing an incision, a wound, or other opening in bodily tissue. In such circumstances, the surgical adhesive 220 can include two or more reactive components that are combined and stored inside the viscous fluid reservoir 200 (FIGS. 2-3), thereby providing a surgical adhesive 220 that is ready for dispensation upon activation of the actuator 110. Particular embodiments of the surgical adhesive 220 may suffer a reduction in quality, storage life, or usefulness if the adhesive 220 was diluted or otherwise premixed with the propellant fluid 320 (FIG. 3). As such, the spray device 100 can isolate the propellant fluid 320 until after the fluids 220 have exited the nozzle, whereupon the propellant is released with sufficient energy to break the adhesive 220 into droplets for spraying. Furthermore, in the embodiment depicted in FIGS. 14-16, the spray device 100 operates as a single-use, disposable instrument that is discarded after dispensing the surgical adhesive 220 during the medical procedure. Accordingly, the spray device 100 can be used in a prompt and sanitary manner without the burden of a clinician having to disassemble and clean parts for subsequent reuse and without the risk of spreading infection from repeated uses with different patients.

Referring to FIG. 14, in this example in which the spray device 100 is used to dispense a surgical adhesive, the spray device 100 can be stored in a surgical storage module 410 (as previously described in connection with FIG. 13). The surgical storage module 410 can be arranged in a surgical instrument rack 420 (FIG. 13) in the operating room so that the spray device 100 is readily accessible by the surgeon or other practitioners during the medical procedure. In this embodiment, the spray device 100 can be prepared for use by removing the spray device 100 from the surgical storage module 410 and removing any individual wrapping (e.g., a sealed pouch to maintain the spray device 100 in a sterilized condition during transport and storage). The user can remove the locking tab 149 so as to free the actuator 110 from the locked, non-activated state. As previously described in connection with FIGS. 1-3, the locking tab 149 can be used to retain the actuator 110 in a non-activated position so as to avoid unintentional dispensation during storage and transport. The locking tab 149 can be arranged on the spray device 100 so that the user can readily remove the locking tab while wearing surgical gloves.

Referring now to FIG. 15, the spray device 100 can be used to deliver the surgical adhesive 220 to a targeted tissue area 50 of a patient's body during a medical procedure. In the non-limiting example illustrated in FIG. 15, the medical procedure can be an abdominoplasty procedure in which an area of skin in the patient's mid-region receives the surgical adhesive 220. For instance, the surgical adhesive 220 can be applied to the targeted tissue area 50 to along the underside of a portion of skin proximate an opening 52 so as to adhere the layer of skin tissue to the underlying tissue. In this particular example of the abdominoplasty procedure, the surgical adhesive 220 can be applied to the targeted tissue area 50 after the surgeon has used a scalpel 55 or other instrument to at least partially remove excess skin from the patient's mid-region. The underside of the skin can be exposed so that the surgical adhesive 220 is deposited to the targeted tissue area 50. Thereafter, the skin layer can be adhered to the underlying tissue while the incision is closed using wound closure techniques such as staples or sutures along the incision. Alternatively, the incision can be closed with the surgical adhesive 220 or another adhesive at the opening 52 without the use of sutures or staples. Such a closure technique may be useful to reduce the amount of post-operative scar marks. It should be understood from the description herein that, in some embodiments, the spray device 100 can be employed in other types of medical procedures in which the surgical adhesive 220 is applied to a targeted area of tissue (e.g., during procedures such as facelifts, mastectomies, breast reduction, breast reconstruction, or the like).

As previously described, the viscous fluid to be dispensed from the spray device 100 can be in the form of a surgical adhesive 220. Some surgical adhesives 220 may have a viscosity from about 200 cP or greater, about 200 cP to about 2,000 cP, about 500 cP to about 1500 cP, and about 500 cP to about 700 cP (measured at 25° C.). Moreover, particular formulations of the surgical adhesive 220 may be moisture sensitive in that exposure to moisture (e.g., during dispensation onto the bodily tissue) causes a chemical process to initiate.

In some embodiments, a suitable adhesive 220 can include the reaction product of: (a) an isocyanate component having an average functionality of at least 2; (b) an active hydrogen component having an average functionality greater than 2.1; and (c) an ionic salt component having an average hydroxyl or amino functionality, or combination thereof, of at least 1. As previously described, these components that mix to form the surgical adhesive 220 can be combined and stored in the viscous fluid reservoir 200. In some embodiments, the spray device 100 can be configured to store the combined components in the reservoir 200 for a storage life of about 6 months to about 18 months, and about 12 months in this embodiment. Upon application of the surgical adhesive 220 to biological tissue in the presence of moisture, the mixture of the components that form the adhesive 220 can crosslink to form a polymer network. The crosslinked network can biodegrade over time, thereby permitting the closed incision to fully heal.

The isocyanate component has an average isocyanate functionality of at least 2, and can be at least 3. The term "average" reflects the fact that the multi-functional isocyanate component can include multiple types of isocyanates, including isocyanates with different functionalities. Suitable isocyanates are hydrophilic, and include those derived from amino acids and amino acid derivatives. Specific examples include lysine di-isocyanate ("LDI") and derivatives thereof (e.g., alkyl esters such as methyl or ethyl esters) and lysine tri-isocyanate ("LTI") and derivatives thereof (e.g., alkyl esters such as methyl or ethyl esters). Dipeptide derivatives can also be used. For example, lysine can be combined in a dipeptide with another amino acid (e.g., valine or glycine).

The active hydrogen component includes one or more active hydrogen reactants. The component has an average functionality greater than 2.1. Again, the term "average" reflects the fact that the active hydrogen component can include multiple types of active hydrogen reactants, including reactants with different functionalities. Some or all of the active hydrogen reactants can have an equivalent weight less than 100. The term "equivalent weight" refers to molecular weight divided by functionality. Thus, for example, glycerol, which has a molecular weight of 92 and a hydroxyl functionality "f" of 3, has an equivalent weight of approximately 31. Examples of suitable active hydrogen components include hydroxyl-functional components, amine-functional components, thiol-functional components, carboxylic acid-functional components, and combinations thereof. In some embodiments, some or all of the functional groups may be primary groups. One class of suitable active hydrogen components includes multi-functional alcohols selected from glycerol, di-glycerol, erythritol, pentaerythritol, xylitol, arabitol, fucitol, ribitol, sorbitol, mannitol, and combinations thereof. Also suitable are hydroxyalkyl derivatives and esters of any of these alcohols such as ethoxylated pentaerythritol. Another class of suitable active hydrogen components includes hydroxyalkyl derivatives of C3-C10 carboxylic or dicarboxylic acids (e.g., dimethylol propionic acid, dimethylol butyric acid, and combinations thereof), and hydroxyalkyl derivatives of C3-C10 hydrocarbons (e.g., trimethylol propane). The active hydrogen component can also be a hydroxalkyl amine (e.g., triethanolamine), a di-, tri-, or tetrakylene glycol, or combination thereof Also suitable are hydroxyl-functional compounds selected from saccharides (e.g., glucose, fructose, sucrose, or lactose), oligosaccharides, polysaccharides, esters thereof, and combinations thereof.

The ionic salt includes one or more hydroxyl and/or amino functional groups. Consequently, it is able to react with the isocyanate-functional component of the reaction mixture, and thereby become covalently incorporated in the adhesive. Examples of suitable salts include ammoniates, halides, sulfonates, phosphonates, carboxylates, and combinations thereof. Specific examples include ammonium halides (e.g., ethyl triethanol ammonium chloride), choline halides (e.g., choline chloride), and combinations thereof.

In some embodiments, the adhesive may further include a catalyst. Examples of suitable catalysts include tertiary amines (e.g., aliphatic tertiary amines) and organometallic compounds (e.g., bismuth salts and zirconium chelates). Specific examples include 1,4-diazabicyclo[2.2.2]octane ("DABCO"), 2,2'dimorpholine diethyl ether ("DMDEE"), dibutyltin dilaurate ("DBTDL"), bismuth 2-ethylhexanoate, and combinations thereof. The amount of catalyst is selected based upon the particular reactants.

Also, in some embodiments, the adhesive may also include a rheology modifying agent in the form of a solvent, a non-volatile diluent, and/or a volatile diluent. Examples of suitable solvents include dimethylsulfoxide (DMSO), dimethylformamide (DMF), tetrahydrofuran (THF), glyme, and combinations thereof Examples of suitable non-volatile diluents include dimethylsulfoxide (DMSO), propylene carbonate, diglyme, polyethylene glycol diacetates, polyethylene glycol dicarbonates, dimethylisosorbide, and combinations thereof. Examples of suitable volatile diluents include hydrocarbons, hydrofluoroalkanes, carbon dioxide, and combinations thereof. A single reagent can perform multiple roles. Thus, for example, DMSO can function as both a solvent and a non-volatile diluent. The amount of the rheology modifying agent is selected based upon the constituents of the adhesive and the particular application for which the adhesive is being used.

Moreover, in some embodiments, the adhesive may also include one or more stabilizers. Examples include antioxidants (e.g., BHT and BHA), water scavengers (e.g., acyl and aryl halides, and anhydrides), Bronsted acids, and the like.

Referring again to FIG. 15, the spray device 100 can be activated by the user to dispense droplets of the surgical adhesive 220. For example, the user can activate the actuator 110 while directing the nozzle 120 toward the targeted tissue site 50. As previously described in connection with FIGS. 7-8 and 12, the actuator 110 can be shifted to the activated position by depressing the actuator 110 (e.g., with the user's finger). The spray device 100 can include the housing 140 that is readily handled by a user wearing surgical gloves (the gloves are removed from view in FIG. 15 to illustrate the user's finger). When the actuator 110 is in the activated position, the surgical adhesive 220 flows from out of the nozzle port 122 while the propellant fluid 320 flows out of different nozzle ports 124 to break the exiting adhesive 220 into droplet formations. Thus, as previously described, the spray device 100 can maintain the surgical adhesive 220 and the propellant fluid 320 in isolation from each other until the fluids 220 and 320 have exited the nozzle ports 122 and 124, respectively.

In some embodiments, the spray device 100 can be equipped a limited volume of the surgical adhesive 220 that approximates an application amount dispensed during a single procedure. For example, the spray device 100 can be equipped with the viscous fluid reservoir 200 that contains the surgical adhesive 220 in a volume of about 3 ml to about 8 ml, about 4 ml to about 6 ml, and about 5 ml in this embodiment. In another example, the spray device 100 may house a selected amount of surgical adhesive that is predetermined to provide a generally continuous spray of adhesive droplets for a period of about 3 seconds to about 15 seconds, about 5 seconds to about 10 seconds, and about 5 seconds in this embodiment. The nozzle 120 of the spray device can be configured to provide a spray pattern of about 3 cm by about 10 cm when the spray device 100 is activated about 10 cm from the target tissue site 50 being coated. In some circumstances, the spray device 100 can apply the spray pattern to provide a total coverage area of about 22 cm by about 28 cm before the spray device 100 is exhausted. After the surgical adhesive 220 is exhausted from its reservoir 200, the entire spray device 100 can be conveniently discarded (as described, for example, in connection with FIG. 16). Accordingly, the spray device 100 can be used and then discarded without reuse in a prompt and sanitary manner.

Still referring to FIG. 15, the surgical adhesive 220 can be applied to the targeted tissue site 50 to adhere a skin layer to another portion of tissue. During dispensation, the surgical adhesive 220 can be delivered in droplet formations having an average droplet size of about 0.5 mm to about 3.0 mm. In such circumstances, the surgical adhesive 220 may have a viscosity of about 200 cP to about 2,000 cP, about 500 cP to about 1500 cP, and about 500 cP to about 700 cP (measured at 25° C.). For example, in this embodiment, the surgical adhesive 220 has a viscosity of about 500 cP (measured at 25° C.). Also, as previously described, the surgical adhesive 220 can be moisture sensitive in that exposure to moisture (e.g., during dispensation onto the bodily tissue) causes some chemical components to crosslink and form a polymer network on the coated surface. In some circumstances, the spray device 200 can be configured to be a disposable and non-reusable device to reduce the likelihood of the nozzle 120 becoming clogged or partially gummed (e.g., due to prolonged dispensing the surgical adhesive 220 having a viscosity in the previously described range and having the previously described moisture-sensitivity characteristics).

Referring now to FIG. 16, some embodiments of the spray device 100 are configured to be a single-use instrument that is discarded after spraying the surgical adhesive 220 onto the targeted tissue site 50 to close the skin opening 52 (FIG. 15). In these embodiments, the spray device 100 can operate as a disposable and non-reusable device that is discarded in a prompt and sanitary manner after delivering the surgical adhesive 220. For example, after the surgical adhesive 220 is exhausted from its reservoir 200 or after the targeted tissue is sufficiently coated, the entire spray device 100 can be conveniently discarded into a discard bin 60. Thus, usage of such embodiments of the spray device 100 does not require a practitioner or medical staff to disassemble parts of the spray device 100 for cleaning or sterilization. Also, because the spray device 100 can be discarded after use with a single patient, the risk of infection can be reduced (e.g., because the device 100 does not operate as an instrument that is reused in subsequent procedures with different patients).

The discard bin 60 may include a disposal container that is used to receive a variety of instruments or materials that are thrown away during the medical procedure. Alternatively, the discard bin may serve as a specialize container that receives the used spray devices 100 for subsequent destruction or recycling by an outside facility. For example, the spray device housing 140 or other components may be recycled in an effort to reduce the amount of materials that are destroyed.

Figure 17:
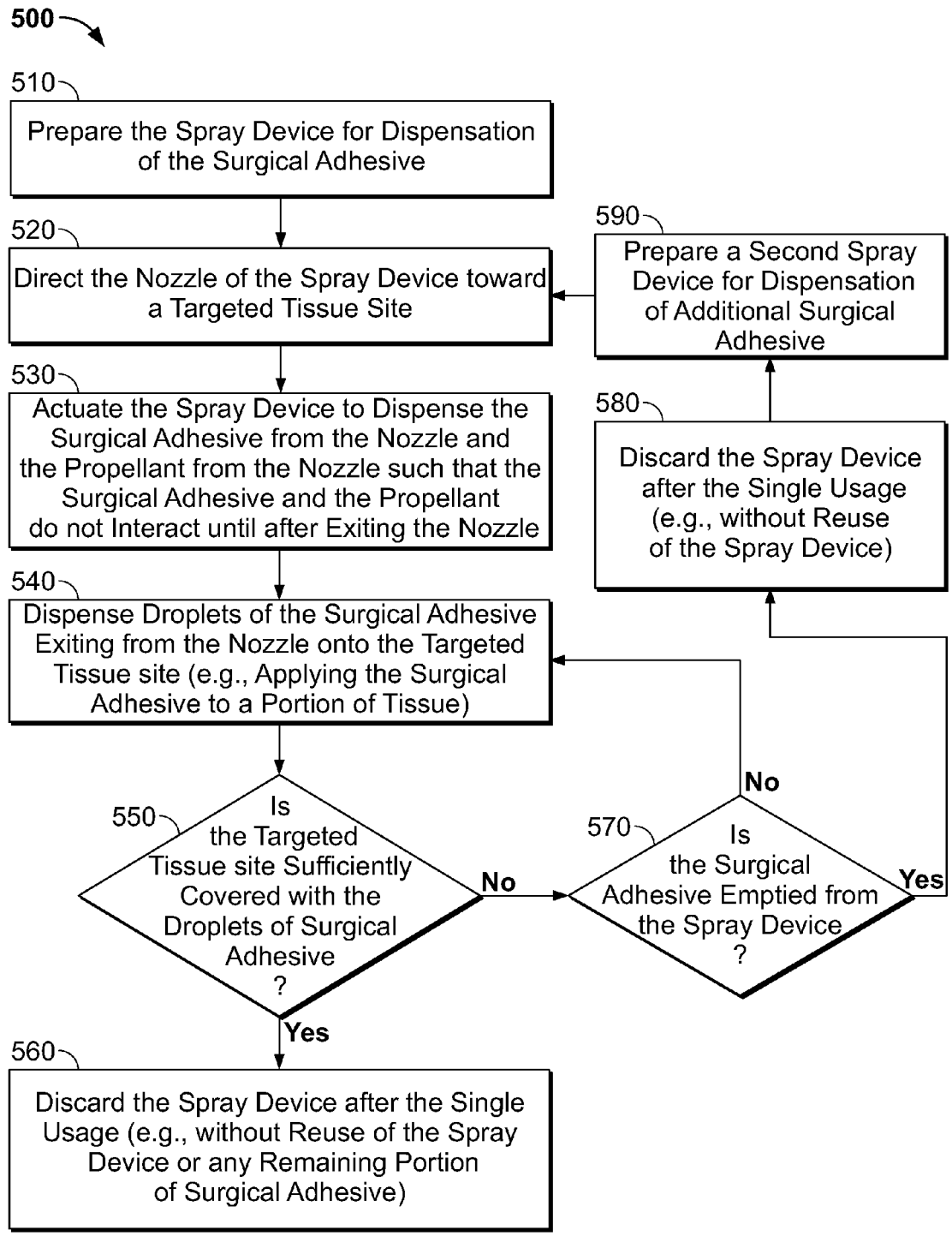
FIG. 17 is a diagram of a process for using a disposable spray device, in accordance with some embodiments.

Referring now to FIG. 17, some embodiments of a process 500 of using a spray device 100 may include discarding the device 100 after a single use. For example, the process 500 can include the operation 510 of preparing the spray device 100 for dispensation of the surgical adhesive 220. This operation 510 may include removing the spray device 100 from its packaging and removing the locking tab 149 (shown in FIG. 14). The process 500 also includes the operation 520 of directing the nozzle 120 of the spray device 100 toward a targeted tissue site. In one embodiment, this operation 520 can include directing the nozzle 120 toward the skin site 50 proximate the skin opening 52 to be closed (e.g., refer to FIG. 15). Next, the process 500 can include the operation 530 of actuating the spray device 100 to dispense the surgical adhesive 220 from the nozzle 120 and to dispense the propellant fluid 320 from the nozzle 120. As previously described, the surgical adhesive 220 and the propellant fluid 320 are isolated from one another and do not interact until after exiting the nozzle ports 122 and 124. In particular, the propellant fluid 320 may act upon the exiting surgical adhesive 220 to cause droplet formations of the surgical adhesive 220.

In operation 540, the droplets of the surgical adhesive 220 are dispensed from the nozzle 120 onto the targeted tissue site. For example, the droplets of the surgical adhesive 220 may be applied to the skin site 50 proximate to the skin opening 52 (e.g., refer to FIG. 15) in order to adhere the skin layer to the underlying tissue.

The process 500 may include the determination 550 of whether the targeted tissue site is sufficiently covered with the droplets of the surgical adhesive 220. If yes, the operation 560 can be implemented to discard the spray device 100 after the single usage (e.g., refer to FIG. 16). In such circumstances, the spray device 100 can be discarded without reuse of the spray device 100 or any remaining portion of the surgical adhesive 220 left in its reservoir 200.

If the determination 550 is no, the process 500 continues to a secondary determination 570 of whether the surgical adhesive 220 is emptied from the spray device 100. If the spray device 100 is not exhausted (e.g., determination 570 is no), the process 500 returns to operation 540 in which the droplets of the surgical adhesive 220 are dispensed from the spray device 100 onto the targeted tissue site.

If the targeted tissue site is not sufficiently covered with the surgical adhesive (e.g., determination 550 is no) but the spray device 100 is exhausted (e.g., determination 570 is yes), the process 500 continues to operation 580. The operation 580 includes discarding the spray device 100 after the single usage (e.g., refer to FIG. 16). In such circumstances, the spray device 100 is exhausted and can be discarded without reuse of the spray device 100. The process 500 can continue to operation 590, in which a second (new) spray device 100 is prepared for dispensation of more surgical adhesive 220 to the targeted tissue site. When the second spray device 100 is prepared, the process 500 returns to operation 520 so that the nozzle 120 of the second spray device 100 is directed toward the targeted tissue site. Thereafter, the process 500 can proceed so that the droplets of the surgical adhesive 220 are dispensed from the second spray device 100 onto the targeted tissue site.

Accordingly, the process 500 can be implemented to dispense the surgical adhesive or other viscous fluid from one or more disposable spray devices 100. In these circumstances, the spray device 200 can be configured to be a disposable and non-reusable device to reduce the likelihood of the nozzle 120 becoming clogged or partially gummed (e.g., due to prolonged dispensing the surgical adhesive 220). Furthermore, the spray device 100 can be used and then discarded in a prompt and sanitary manner.

Figure 18:
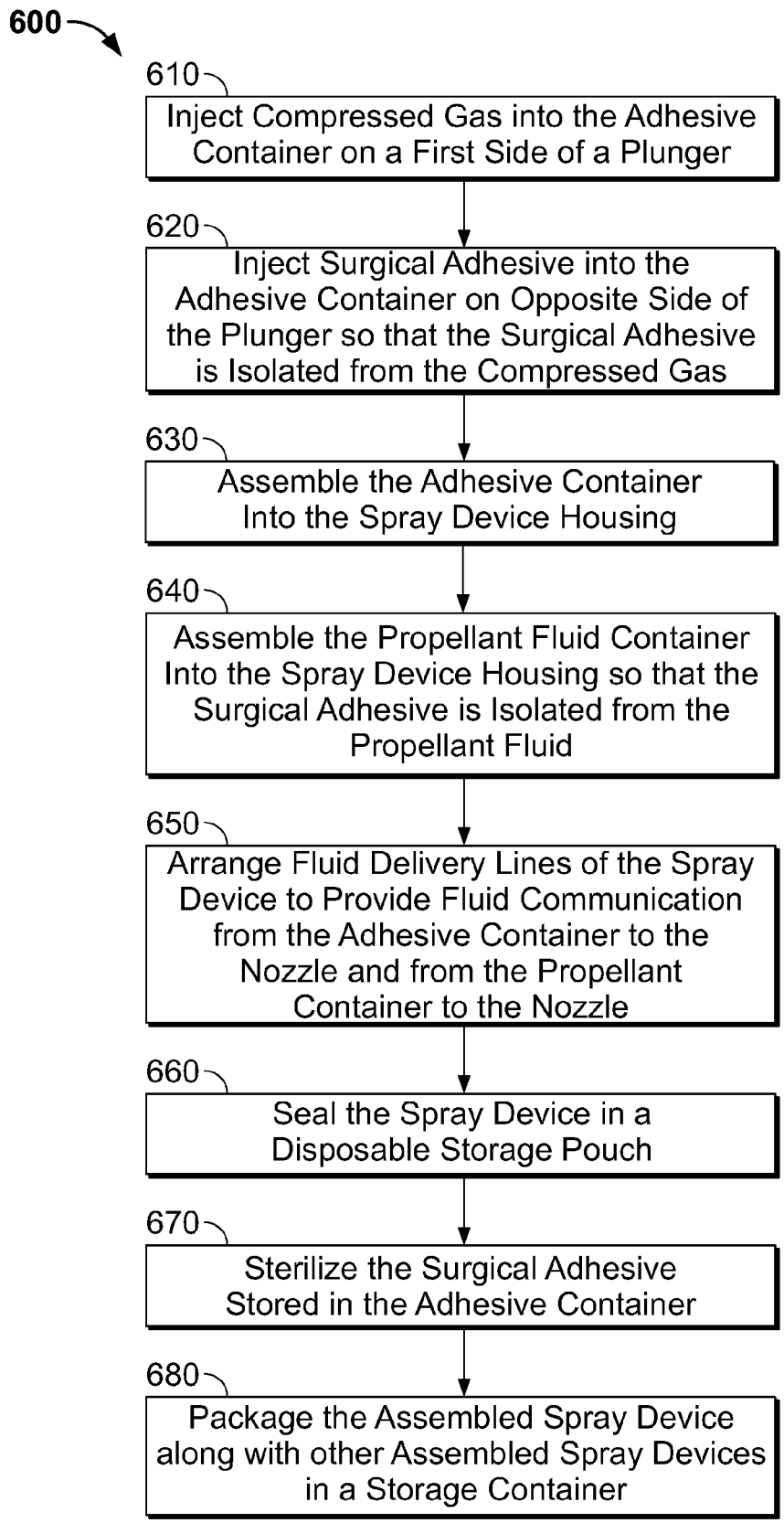
FIG. 18 is a diagram of a process for manufacturing a spray device, in accordance with some embodiments.

Referring now to FIG. 18, a process 600 for manufacturing one or more of the spray devices 100 may include preparing the adhesive reservoir 200 (FIGS. 2-3) and assembling the internal components with the spray device housing 140 (FIGS. 1-3). In this embodiment, the process 600 includes the operation 610 of injecting the compressed gas 240 (FIG. 3) into a container (e.g., reservoir 200) on a first side of a plunger 230. As previously described in connection with FIG. 3, the compressed gas 240 may operate as a gas spring that urges the movable plunger 230 against the surgical adhesive 220 or other viscous fluid. The reservoir container 200 may include the fill port 245 that is dedicated for receiving the compressed gas 240. In operation 620, the surgical adhesive 220 is injected in the container (e.g., reservoir 200) on an opposite side of the plunger 230 so that the surgical adhesive 220 is isolated from the compressed gas 240 by the plunger 230 therebetween. In some embodiments, the surgical adhesive 220 can be injected at a fill pressure of about 40 psi so as to overcome the check valve in the fill port 225 and to move plunger 230 downward to increase the interior space for the adhesive 220 (FIG. 3). In these circumstances, the compressed gas 240 can be injected at a predetermined pressure so that resulting pressure on the adhesive 220 during storage is about 20 psi. It should be understood that, in some embodiments, the operation 610 may occur after the operation 620 so that the adhesive 220 is injected before the compressed gas 240.

The process 600 can also include the operation 630 of assembling the adhesive container (e.g., reservoir 200 depicted in FIGS. 2-3) into the spray device housing 140. For example, the reservoir 200 can be inserted into the interior space 142 of the base structure 141, as shown in FIG. 2. Furthermore, the process 600 can include the operation 640 of assembling the propellant fluid container (e.g., reservoir 300 as depicted in FIGS. 2-3) into the spray device housing 140 so that the surgical adhesive 220 is isolated from the propellant fluid. As shown in FIG. 2, the reservoir 300 can be inserted into the interior space 143 of the base structure 141. In this embodiment, the propellant fluid 320 in the reservoir 300 is separated from the surgical adhesive 220 prior to dispensing from the nozzle ports 122 and 124.

In operation 650, the fluid delivery lines are arranged to provide fluid communication from the adhesive container (e.g., reservoir 200) to the nozzle 120 and from the propellant container (e.g., reservoir 300) to the nozzle 120. For example, the actuator 110 and the propellant conduits 114 (FIGS. 2-3) can be arranged so that the propellant reservoir 300 is in fluid communication with the nozzle 120 when the release valve 335 is selectively opened. Also, in this embodiment, the output conduit 132 (FIG. 3) is pre-assembled with the nozzle 120 so that the adhesive reservoir 200 is already in fluid communication with the nozzle 120.

The process 600 may also include the operation of sealing the assembled spray device 100 into a disposable storage pouch. The disposable storage pouch can be used to reduce the likelihood of contamination during storage or transport. In some circumstances, the storage pouch can also contain instructions for use of the spray device 100. Alternatively, the storage pouch can include instructions printed onto a surface of the storage pouch.

In operation 670, the spray device 100 can undergo a sterilization process so that the surgical adhesive 220 therein is sterilized. In one example, the surgical adhesive 220 can be sterilized using a gamma radiation device after the spray device 100 is sealed in the storage pouch. Furthermore, the process 600 can include the operation 680 of packaging the assembled spray device 100 in a storage container along with other spray devices 100. For example, one or more spray devices 100 can be part of a packaged system 400 (FIG. 13) that permits the sprays devices 100 to be readily available to the surgeon or other practitioner in a safe and reliable manner. The set of spray devices 100 may be arranged in a surgical storage module 410 (FIG. 13), which can be readily received from a supplier and then fit into the surgical instrument rack 425 (FIG. 13) for immediate or subsequent use in a surgical environment. Such a configuration can reduce the burden of staff workers responsible for material handling and inventory restocking. As previously described, some embodiments of the spray device 100 may have a storage life of about 6 months to about 18 months, and about 12 months in this embodiment. In some circumstances, the spray devices 100, the storage container, or both may be labeled with an expiration date so as to notify the practitioner of the estimated useful life of each spray device 100.

A number of embodiments of the invention have been described. Nevertheless, it will be understood that various modifications may be made without departing from the spirit and scope of the invention. Accordingly, other embodiments are within the scope of the following claims.

What is claimed is:

1. A spray device for dispensing droplets of a viscous fluid, comprising:
    a housing defining an interior space to receive a supply of a propellant fluid and a supply of a viscous fluid;
    a first container arranged in a portion of the housing to maintain the supply of the viscous fluid in isolation from propellant fluid, wherein the first container comprises: an exit port through which the viscous fluid is adapted to exit, a movable plunger device in an interior space of the first container that is biased toward the viscous fluid, and a least a second port positioned on the first container so as to face a different direction than the exit port; and
    a nozzle device to spray droplets of the viscous fluid toward a targeted site, the nozzle device being fixedly coupled to the portion of the housing that receives the first container and being in fluid communication with the first container in the housing such that the viscous fluid interacts with the propellant fluid only after exiting the nozzle device.

2. The device of claim 1, wherein the viscous fluid comprises a surgical adhesive.

3. The device of claim 1, further comprising a second container arranged in the housing to maintain the supply of the propellant fluid in isolation from the viscous fluid, wherein the second container is in fluid communication with at least one propellant dispensation port of the nozzle device, and the first container is in fluid communication with at least one viscous fluid dispensation port of the nozzle device.

4. The device of claim 3, further comprising an actuator that is movable to an activated position so as to contemporaneously release both the propellant fluid from the second container and the viscous fluid from the first container.

5. A spray device packaging system, comprising:
    a surgical storage module defining an interior space; and
    a plurality of surgical adhesive spray devices each contained in individual trays or pouches and arranged fully within the interior space of the storage module, each of the spray devices comprising:
        a housing, a portion of the housing containing a supply of a propellant fluid and a supply of surgical adhesive;
        an actuator movably coupled to the housing and being adjustable from a first position to a second position so as to cause continuous dispensation of both the surgical adhesive and the propellant fluid while the actuator is fixed in the second position; and
        a nozzle device to spray droplets of the surgical adhesive in response to movement of the actuator, wherein the nozzle device is mounted in a fixed position relative to the portion of the housing that that contains the supply of the propellant fluid and the supply of surgical adhesive such that the supply of the propellant fluid and the supply of surgical adhesive contained in the housing are carried together with the nozzle device.

6. The system of claim 5, wherein the surgical storage module has a height of about 14 cm, a width of about 12.5 cm, and a depth of about 14 cm, and the surgical storage module receives five of the surgical spray devices.

* * * * *